(12) United States Patent
Sekhavat

(10) Patent No.: US 11,696,883 B2
(45) Date of Patent: *Jul. 11, 2023

(54) COMPOSITIONS FOR REDUCING HAIR LOSS AND/OR INCREASING HAIR REGROWTH

(71) Applicant: Triple Hair Inc., Montreal (CA)

(72) Inventor: Houfar Sekhavat, Dieppe (CA)

(73) Assignee: Triple Hair Inc., Dieppe (CA)

( * ) Notice: Subject to any disclaimer, the term of this patent is extended or adjusted under 35 U.S.C. 154(b) by 0 days.

This patent is subject to a terminal disclaimer.

(21) Appl. No.: 15/167,778

(22) Filed: May 27, 2016

(65) Prior Publication Data

US 2016/0346183 A1 Dec. 1, 2016

Related U.S. Application Data

(63) Continuation-in-part of application No. 14/917,501, filed as application No. PCT/CA2015/000327 on May 22, 2015, now Pat. No. 10,470,992.

(60) Provisional application No. 62/002,397, filed on May 23, 2014.

(51) Int. Cl.
| | |
|---|---|
| *A61Q 7/00* | (2006.01) |
| *A61K 9/00* | (2006.01) |
| *A61P 17/14* | (2006.01) |
| *A61K 8/49* | (2006.01) |
| *A61K 8/37* | (2006.01) |
| *A61K 8/63* | (2006.01) |
| *A61K 45/06* | (2006.01) |
| *A61K 8/02* | (2006.01) |
| *A61K 8/04* | (2006.01) |
| *A61K 31/58* | (2006.01) |
| *A61K 31/5575* | (2006.01) |
| *A61K 8/36* | (2006.01) |
| *A61K 31/506* | (2006.01) |

(52) U.S. Cl.
CPC .......... *A61K 8/4953* (2013.01); *A61K 8/0204* (2013.01); *A61K 8/046* (2013.01); *A61K 8/361* (2013.01); *A61K 8/37* (2013.01); *A61K 8/63* (2013.01); *A61K 31/506* (2013.01); *A61K 31/5575* (2013.01); *A61K 31/58* (2013.01); *A61K 45/06* (2013.01); *A61P 17/14* (2018.01); *A61Q 7/00* (2013.01); *A61K 9/0014* (2013.01); *A61K 2800/592* (2013.01)

(58) Field of Classification Search
CPC .......... A61K 9/0014; A61Q 7/00; A61P 17/14
See application file for complete search history.

(56) References Cited

U.S. PATENT DOCUMENTS

| | | | |
|---|---|---|---|
| 4,746,674 A | 5/1988 | Pierpaoli et al. | |
| 5,407,944 A * | 4/1995 | Goldman | A61K 8/40 514/256 |
| 6,013,279 A | 1/2000 | Klett-Loch | |
| 6,030,948 A | 2/2000 | Mann | |
| 6,281,241 B1 | 8/2001 | Elsner | |
| 6,818,226 B2 | 11/2004 | Reed et al. | |
| 6,828,458 B2 | 12/2004 | Sovak et al. | |
| 7,704,533 B2 | 4/2010 | Bruning et al. | |
| 7,834,210 B2 | 11/2010 | Gupta | |
| 8,017,645 B2 | 9/2011 | Schmid | |
| 8,062,648 B2 | 11/2011 | Schmid | |
| 8,163,311 B2 | 4/2012 | Bruning et al. | |
| 8,470,833 B2 | 6/2013 | Hu et al. | |
| 8,481,015 B2 | 7/2013 | Oblong et al. | |
| 8,551,462 B2 | 10/2013 | Goldstein et al. | |
| 8,591,874 B2 | 11/2013 | Oblong et al. | |
| 8,758,733 B2 | 6/2014 | Ahluwalia | |
| 8,802,117 B2 | 8/2014 | Morganti | |
| 8,871,773 B2 | 10/2014 | Hu et al. | |
| 8,877,762 B2 | 11/2014 | Hu et al. | |
| 2003/0199590 A1 | 10/2003 | Cagle | |
| 2009/0098069 A1 | 4/2009 | Vacca | |
| 2011/0183016 A1 | 7/2011 | Mailland et al. | |
| 2011/0195039 A1 | 8/2011 | Isaacs | |
| 2012/0277249 A1 | 11/2012 | Anderson et al. | |

(Continued)

FOREIGN PATENT DOCUMENTS

| | | |
|---|---|---|
| CA | 2 315 395 A1 | 7/1999 |
| CA | 2 339 231 A1 | 2/2000 |

(Continued)

OTHER PUBLICATIONS

Goldman (U.S. Pat. No. 5,407,944) and Peytavi (A randomized double-blind placebo-controlled pilot study to assess the efficacy of a 24-week topical treatment by latanoprost 0.1% on hair growth and pigmentation in healthy volunteers with androgenetic alopecia, Journal of the Amercan Academy of Dermatology, vol. 66, Issue 5, 2012, pp. 794-800).*

International PCT Search Report dated Jul. 27, 2015 from corresponding International Application No. PCT/CA2015/000327, 4 pages.

International PCT IPRP dated Nov. 27, 2016 from corresponding International Application No. PCT/CA2015/000327, 5 pages.

Canadian Office Action dated Oct. 19, 2015, 3 pages.

Response to Canadian Office Action dated Oct. 22, 2015, including amended claims, 4 pages.

Canadian Notice of Allowance for CA 2,903,734 dated Nov. 30, 2015, 1 pages.

Granted claims from Canadian Patent No. 2,903,734 including cover page, 4 pages.

(Continued)

*Primary Examiner* — Theodore R. Howell
(74) *Attorney, Agent, or Firm* — Finnegan, Henderson, Farabow, Garrett & Dunner, LLP

(57) ABSTRACT

The invention relates to a composition comprising 2% to 5% minoxidil, 0.01% to 15% of a 5α-reductase inhibitor or an androgen receptor antagonist, and 0.01% to 15% of a prostaglandin analogue. In one embodiment, the prostaglandin analogue is latanoprost. In a preferred embodiment, the composition comprises 5% minoxidil, 0.1% finasteride and 0.03% latanoprost. The invention also relates to the use of the said composition to reduce hair loss and/or increase regrowth of hair in a human subject.

13 Claims, 115 Drawing Sheets

(56) References Cited

U.S. PATENT DOCUMENTS

| | | |
|---|---|---|
| 2016/0213590 A1 | 7/2016 | Sekhavat |
| 2017/0100319 A1 | 4/2017 | Sekhavat |

FOREIGN PATENT DOCUMENTS

| | | | |
|---|---|---|---|
| CA | 2 309 373 A1 | 11/2000 | |
| CA | 2 309 413 A1 | 11/2000 | |
| CA | 2 392 620 A1 | 6/2001 | |
| CA | 2 206 530 C | 10/2001 | |
| CA | 2 552 607 A1 | 7/2005 | |
| CA | 2 558 150 A1 | 9/2005 | |
| CA | 2 579 784 A1 | 3/2006 | |
| CA | 2 608 031 A1 | 11/2006 | |
| CA | 2 732 582 A1 | 2/2010 | |
| CA | 2 765 284 A1 | 12/2010 | |
| CA | 2 819 859 A1 | 6/2012 | |
| WO | WO 2000/048559 A2 | 8/2000 | |
| WO | WO 2011/031990 A1 | 3/2011 | |
| WO | WO 2013/078259 A2 | 5/2013 | |
| WO | WO 2013/142295 A1 | 9/2013 | |
| WO | WO 2013/181487 A2 | 12/2013 | |

OTHER PUBLICATIONS

Uno, et al., "Effect of Latanoprost on Hair Growth in the Bald Scalp of the Stump-tailed Macacque: a Pilot Study", Abstract, *Acta Derm. Venereol*, 2002:82(1):7-12 (1 page).

http://www.medicalwellnesscenter.com, Jun. 2013 (10 pages), including http://xenicalwtloss.hypermart.net/MINOXIDILSHAMPOOHairLossPrescriptionINDEX . . . (Jun. 2013) (1 page), total 11 pages.

Levy, et al. "Female Pattern Alopecia: Current Perspectives", *Int. J. Women's Health*, 2013, 5:541-556, Aug. 2013, 19 pages.

http://www.belgraviacentre.com, Belgravia Centre "Japan Delays Dutasteride Drug for Male Pattern Hair Loss", retrieved May 2016, 8 pages.

GlaxoSmithKline, "GlaxoSmithKline Publishes Japanese Dutasteride Hair Loss Study Results", Sep. 2014, 3 pages.

http://hairlosscure2020.com, "The End of Hair Loss and Balding by 2020," Brief Items of Interest, May 2016, 9 pages.

Hamishehkar et al., "Histological Assessment of Follicular Delivery of Flutamide by Solid Lipid Nanoparticles: Potential Tool for the Treatment of Androgenic Alopecia," *Drug Dev. Ind. Pharm.* Jun. 2016;42(6):846:53, 2 pages.

Indian Office Action dated Jun. 15, 2018 in counterpart Indian application No. 201627015405 (6 pages).

European Search Report and Supplemental Search Report dated Oct. 18, 2016 in counterpart European Application No. 15795754 (10 pages).

Response to European Search Report dated May 16, 2017 in counterpart European Application No. 15795754 (9 pages).

McElwee et al., "Promising Therapies for Treating and/or Preventing Androgenic Alopecia," Skin Therapy Letter vol. 17(6), Jun. 2012 (8 pages).

Chinese Office Action dated Nov. 16, 2017, 5 pages.

Chinese Office Action dated Mar. 27, 2018, 5 pages.

Chinese Office Action dated Nov. 16, 2017, 7 pages (English translation).

Chinese Office Action dated Mar. 27, 2018, 6 pages (English translation).

\* cited by examiner

COMPOSITIONS FOR REDUCING HAIR LOSS AND/OR INCREASING HAIR REGROWTH

CROSS-REFERENCE TO RELATED APPLICATIONS

This application is a continuation-in-part of U.S. patent application Ser. No. 14/917,501, which is a continuation of PCT/CA2015/000327 filed May 22, 2015 which in turn claims priority to US provisional patent application 62/002,397, filed May 23, 2014, this application also claims priority to Canadian Patent Application Ser. No. 2903734, filed Sep. 2, 2015. The disclosure of the above applications are hereby incorporated herein by reference.

FIELD OF INVENTION

The inventor has developed a composition comprising minoxidil, finasteride and a prostaglandin analogue that shows improved properties in terms of reducing hair loss and increasing hair regrowth when compared to conventional therapies, such as the topical application of a solution of 5% minoxidil.

BACKGROUND

Androgenetic alopecia (AGA) is hair loss (at scalp level) caused by the thinning of hair follicles. It is very common in men between the age of 19 and 70 years. Notably, more than 50% of Caucasian men in their fifties are affected by it. Women's hair loss mostly becomes an issue after menopause.

Alopecia occurs as a result of the transformation of terminal hair follicles, which are large, thick and pigmented, to vellus hair follicles, which are short, thin and non-pigmented. This process is known as miniaturization. Dihydrotestoterone (DHT) is believed to play a role in such a process. Testosterone is converted to DHT in the cells by the enzyme, 5α-reductase. This enzyme is found in various tissues including the hair follicle. Decreasing the levels of DHT in the hair follicle can prevent or slow down the miniaturization process. This can be accomplished either by inhibiting the conversion of testosterone to DHT or by competing with testosterone or DHT for the androgen receptors through the use of an androgen receptor antagonist.

Individuals affected by androgenetic alopecia (AGA) show a diminution of their self-esteem that can effect negatively many facets of their lives. The inventor has developed a composition for topical administration comprising minoxidil, finasteride and a prostaglandin analogue is effective in reducing hair loss and increasing hair regrowth.

There are several hair loss prevention products on the market. By way of example, minoxidil has been in use since the 1990s in topical form at 2% concentration (without prescription) and at 3% and 5% concentration (with prescription). While studies demonstrate the efficiency of 5% minoxidil over the 2% concentration, minoxidil is less than 40% effective in promoting regrowth of the hair. Minoxidil is considered the topical gold standard available for treatment of hair loss.

Another hair loss prevention product is finasteride. It is administered orally usually at a dosage of 1 mg/day. There are a number of side effects associated with the administration of finasteride including lowered libido, impotence, ejaculation disorders, allergic reactions, testicular pain, male infertility, male breast cancer and depression. At higher concentrations (5 mg), finasteride can cause benign prostate hyperplasia.

Latanoprost, a $PGF_{2\alpha}$ prostaglandin analog, is widely used in ophthalmology to treat open angle glaucoma and ocular hypertension. One of its side effects has been an augmentation of periocular hirsuteness, which includes a surge in the thickness, length and pigmentation of eyelashes which is to be distinguished from hair growth. Some of its other adverse effects are erythema, folliculitis, sensation of burning and erysipelas. A latanoprost ophthalmic solution has a concentration of 0.005%. It should be noted that scalp hair follicles and eyelash follicles are not identical and one cannot simply extrapolate from a drug effect on one type of hair to another.

SUMMARY

The inventor has developed a composition comprising minoxidil, either a 5α-reductase inhibitor or an androgen receptor antagonist, and a prostaglandin analogue for topical application to the scalp reduces hair loss and increases hair regrowth. Such a composition shows superior improvements to those seen for each of the components of the composition taken individually and the results obtained to date suggest that the improvements may be superior to those of the sum of the said components.

The invention relates to a composition comprising 2% to 5% minoxidil, 0.01% to 15% of a 5α-reductase inhibitor or an androgen receptor antagonist, and 0.01% to 15% of a prostaglandin analogue.

In a preferred embodiment, the invention relates to a composition comprising 2% to 5% minoxidil, 0.01% to 15% finasteride and 0.01% to 15% of a prostaglandin analogue. In one embodiment, the prostaglandin analogue is latanoprost. In another embodiment, the composition comprises 5% minoxidil, 0.1% finasteride and 0.03% latanoprost. The invention also relates to the use of a composition comprising 2% to 5% minoxidil, 0.01% to 15% finasteride and 0.01% to 15% of a prostaglandin analogue to reduce hair loss and/or increase regrowth of hair in a human subject.

BRIEF DESCRIPTION OF THE FIGURES

FIGS. 1A and 1B show the scalp before treatment on the first day of month 1, FIGS. 1C and 1D show the scalp on month 2, FIGS. 1E and 1F on month 3, FIGS. 1G and 1H on month 4, FIGS. 1I and 1J on month 5 and FIGS. 1K and 1L on month 6;

FIGS. 2A and 2B show the scalp before treatment on the first day of month 1, FIGS. 2C and 2D show the scalp on month 2, FIGS. 2E and 2F on month 3, FIGS. 2G and 2H on month 4, FIGS. 2I and 2J on month 5 and FIGS. 2K and 2L on month 6;

FIGS. 3A and 3B show the scalp before treatment on the first day of month 1, FIGS. 3C and 3D show the scalp on month 2, FIGS. 3E and 3F on month 3, FIGS. 3G and 3H on month 4, FIGS. 3I and 3J on month 5 and FIGS. 3K and 3L on month 6;

FIGS. 4A and 4B show the scalp before treatment on the first day of month 1, FIGS. 4C and 4D show the scalp on month 2. FIGS. 4E and 4F on month 3, FIGS. 4G and 4H on month 4, FIGS. 4I and 4J on month 5 and FIGS. 4K and 4L for month 6;

FIGS. 5A and 5B show the scalp before treatment on the first day of month 1, FIGS. 5C and 5D show the scalp on month 2, FIGS. 5E and 5F on month 3, FIGS. 5G and 5H on month 4, FIGS. 5I and 5J on month 5 and FIGS. 5K and 5L on month 6;

FIGS. 6A and 6B show the scalp before treatment on the first day of month 1, FIGS. 6C and 6D show the scalp on month 2, FIGS. 6E and 6F 6C on month 3, FIGS. 6G and 6H on month 4, FIGS. 6I and 6J on month 5 and FIGS. 6K and 6L on month 6;

FIGS. 7A and 7B show the scalp before treatment on the first day of month 1, FIG. 7C shows the scalp on month 2, FIG. 7D on month 3, FIG. 7E on month 4, FIG. 7F on month 5 and FIG. 7G on month 6;

FIGS. 8A and 8B show the scalp before treatment on the first day of month 1, FIGS. 8C and 8D show the scalp on month 2, FIGS. 8E and 8F on month 3, FIGS. 8G and 8H on month 4, FIGS. 8I and 8J on month 5 and FIGS. 8K and 8L on month 6;

FIGS. 9A and 9B show the scalp before treatment on the first day of month 1. FIGS. 9C and 9D show the scalp on month 2, FIGS. 9E and 9F on month 3. FIGS. 9G and 9H on month 4, FIGS. 9I and 9J on month 5 and FIGS. 9K and 9L on month 6;

FIGS. 10A to 10L are a series of photographs showing the scalp of participant 10 prior to treatment and at intervals throughout the course of a six month treatment with a solution of 0.03% latanoprost only. FIGS. 10A and 10B show the scalp before treatment on the first day of month 1, FIGS. 10C and 10D show the scalp on month 2, FIGS. 10E and 10F on month 3, FIGS. 10G and 10H on month 4, FIGS. 10I and 10J on month 5 and FIGS. 10K and 10L on month 6.

DETAILED DESCRIPTION OF THE INVENTION

Figure 1A:
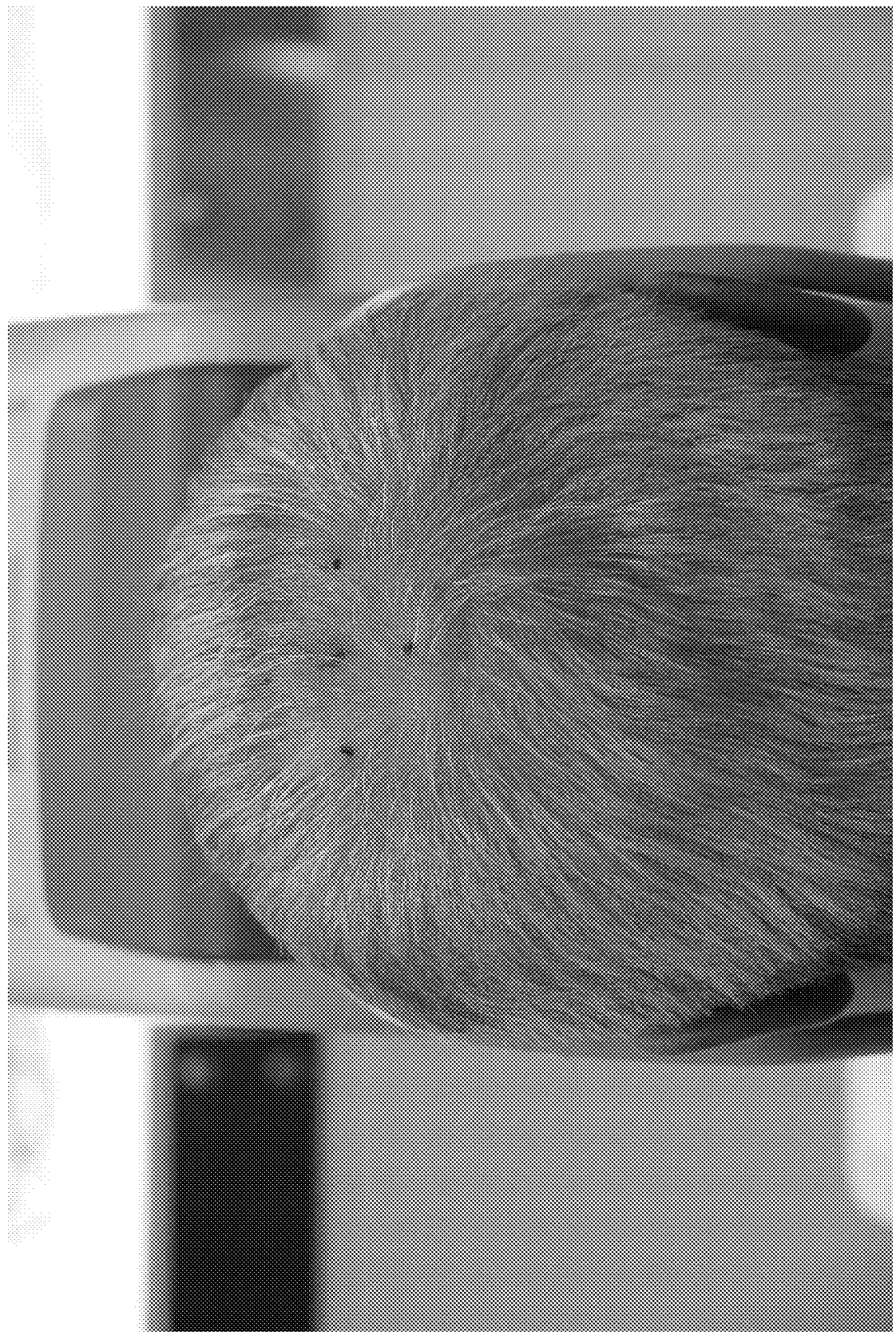
FIGS. 1A to 1L are a series of photographs showing the scalp of participant 1 prior treatment and at intervals throughout the course of a six month treatment with a composition of the invention.

The invention relates to a composition comprising minoxidil, a 5α-reductase inhibitor or an androgen receptor antagonist and a prostaglandin analog which shows improved properties for the reduction of hair loss and for the increase of hair regrowth in human subjects, when compared to each component taken alone.

Minoxidil or (6-(1-pipedidinyl)-2,4-pyrimidinediamine 3-oxide) has the following structural formula:

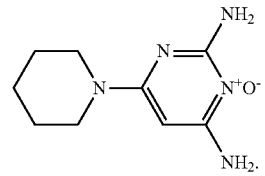

Minoxidil is a crystalline solid which has a solubility in mg/ml of 75 in propylene glycol, of 44 in methanol, of 29 in ethanol, of 6.7 in 2-propanol, of 6.5 in DMSO, of 2.2 in water, of 0.5 in chloroform, and of <0.5 in acetone. Minoxidil has a pKa of 4.61.

Inhibitors of 5α-reductase inhibit the conversion of testosterone to DHT. The 5α-reductase enzyme has three different isoforms, type I, type D or type III. The inhibitors can inhibit one or more of the these isoforms. The type II form is found predominantly in the hair follicles. Finasteride is an example of a 5α-reductase type II and III inhibitor. While the composition tested comprises finasteride, it is hypothesized that other 5α-reductase inhibitors can also be used. By way of example, other suitable 5α-reductase inhibitors include dutasteride ((5α, 17β)-N-{2,5-Bis(tris-fluoromethyl)phenyl}-3-oxo-4-azaandrost-1-ene-17-carboxamide), izonsteride ((4aR,10bR)-8-[(4-ethyl-1,3-benzothiazol-2-yl)sulfanyl]-4,10b-dimethyl-1,4,4a,5,6,10b-hexahydrobenzo[f] quinolin-3(2H)-one), epristeride (17-(tert-butylcarbamoyl)androsta-3,5-diene-3-carboxylic acid), lapisteride (N-[1-(4-methoxyphenyl)-1-methylethyl]-3-oxo-4-aza-5α-androst-1-ene-17β-carboxamide), turosteride ((4aR,4bS,6aS,7S,9aS,9bS,11aR)-1,4a,6a-trimethyl-2-oxo-N-(propan-2-yl)-N-(propan-2-ylcarbamoyl)hexadecahydro-1H-indeno[5,4-f]quinoline-7-carboxamide) and alfatradiol (Estra-1,3,5(10)-triene-3,17α-diol). Duasteride is an inhibitor of all three forms of 5α-reductase. Lapisteride and izonsteride are types I and II inhibitors. Epristeride and turosteride are type II inhibitors.

Finasteride or ((5α,17β)-N-(1,1-Dimethylethyl)-3-oxo-4-azaandrost-1-ene-17-carboxamide) is an example of a 5α-reductase inhibitor and has the following structural formula:

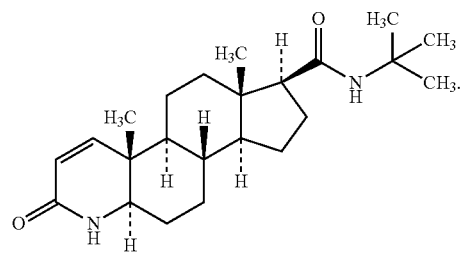

Finasteride is conventionally administered orally at a daily dose of 1 mg.

Finasteride is an anhydrous crystalline solid. Finasteride is freely soluble in chloroform, DMSO, ethanol, methanol, n-propanol; sparingly soluble in propylene glycol, polyethylene glycol 400; and very slightly soluble in 0.1N HCl and 0.1N NaOH. Finasteride is not soluble in water.

Antagonists of the androgen receptors work by competing with testosterone and DHT for androgen receptor binding leading to reduced levels of DHT. Various antagonists of the androgen receptors are known. By way of example, these include flutamide (2-methyl-N-[4-nitro-3-(trifluoromethy)) phenyl]-propanamide) and topilutamide (2-Hydroxy-2-methyl-N-[4-nitro-3-(trifluoromethyl)phenyl]-3-[2,2,2-trifluoroacetyl)amino]propanamide), which is also known as fluridil. It is surmised that while the androgen receptor antagonists have a different mechanism of action than the 5α-reductase inhibitors, they share a common effect of leading to decreased levels of DHT in the hair follicle and thus could be used in the hair composition of the invention.

Latanoprost or ((5Z)-7-[(1R,2R,3R,5SO-3,5-Dihydroxy-2-[(3R)-3-hydroxy-5-phenylpentyl] cyclopentyl]-5-heptenoic acid 1-methylethyl ester) has the following structural formula:

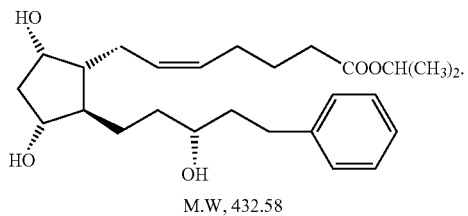

M.W. 432.58

Latanoprost is an oil. Latanoprost is very soluble in acetonitrile; freely soluble in acetone, ethanol, ethyl acetate, isopropanol, methanol and octanol. It is practically insoluble in water.

Prostaglandins regulate a number of physiological functions. It has been found that most hair cell types are endowed with prostaglandin metabolism machinery and are thus able to produce $PGE_2$ and/or $PGF_{2\alpha}$. The epithelial part of the hair bulb is the main source of prostaglandin synthesis and interconversion. From Colombe et al. (*Prostaglandin Metabolism in Human Hair Follicle*, Exp Dermatol. 2007 September, 16(9): 762 to 769) and as minoxidil has also been found to enhance prostaglandin endoperoxide synthase-1 (PGHS-1) activity, this suggests that prostaglandins are involved in hair growth and differentiation control and that there is a link between prostaglandin synthesis and hair growth. Minoxidil has been demonstrated to be a potent activator of purified PGHS-1 by assaying oxygen consumption in prostaglandin $PGE_2$ production suggesting that the mechanism beyond the hair-growth stimulating effect of minoxidil is stimulation of $PGE_2$ synthesis (Michelet et al., *Activation of Cytoprotected Prostaglandin Synthase-1 by Minoxidil as a Possible Explanation for Its Hair Growth-Stimulating Effect*, J. Invest Dermatol 1997: 108: 205-209). This has been confirmed by the role of PGHS-2 in the control of hair cycle (Muller-Decker et al., *Expression of Cyclo-Oxygenase Isozymes During Morphogenesis and Cycling of Telage Hair Follicles in Mouse Skin*, J. Invest Dermatol 2003: 121: 661-668). It has been shown that the human hair follicle can sustain a complete $PGE_2$ and $PGF_{2\alpha}$ metabolism. Human hair follicle express (i) mPGES-1, mPGES-2 and cPGES which catalyse $PGE_2$ synthesis from $PGH_2$, (ii) AKR1C3/PGFS which converts $PGH_2$ into $PGF_{2\alpha}$ and (iii) CDR1 and AKR1C1 aldo-ketoreductase, which could control $PGE_2/PGF_{2\alpha}$ interconversion. As such, it has been shown that human hair follicles appear fully enzymatically equipped to self-process prostaglandin synthesis and metabolism, meaning $PGE_2$ and $PGF_{2\alpha}$ could be produced and inter-converted by hair follicles. While the composition tested comprised latanoprost, a $PGF_{2\alpha}$ prostaglandin analogue, it is surmised that other prostaglandin analogues can also be used given the role played by prostaglandin in hair growth and differentiation. By way of example, other suitable prostaglandin analogues include travoprost, bimatoprost, tafluprost and unoprostone.

The composition of the invention comprises 2% to 5% minoxidil, 0.01% to 15% of a 5α-reductase inhibitor of an androgen receptor antagonist and 0.01% to 15% of a prostaglandin analogue. In a preferred embodiment, the composition comprises 2% to 5% minoxidil, 0.01% to 5% finasteride and 0.01% to 5% of a prostaglandin analogue. In a more preferred embodiment, the composition comprises 5% minoxidil, 0.5% finasteride and 0.1% of a prostaglandin analogue. In a yet other preferred embodiment, the prostaglandin analogue is latanoprost, travoprost, bimatoprost, tafluprost or unoprostone. In a further preferred embodiment, the prostaglandin analogue is latanoprost. In an even more preferred embodiment, the composition comprises 5% minoxidil, 0.1% finasteride and 0.03% latanoprost as set out in Table 1 below.

In order to demonstrate the improved properties of a composition suitable for topical application comprising minoxidil, finasteride and a prostaglandin analogue, latanoprost, the composition was compared to compositions comprising 5% minoxidil only, 0.1% finasteride only and 0.03% latanoprost only. The various compositions were prepared as follows.

Example 1

Preparation of Composition Comprising Finasteride, Latanoprost and Minoxidil

In order to prepare the composition, latanoprost was diluted to obtain a concentration of 10,000 mcg/ml of solute on in absolute ethyl alcohol, and prepared as a stock solution and kept in a freezer to enhance stability (−20° C.). Absolute ethyl alcohol was mixed with propylene glycol and heated to 55°-65° C. Minoxidil powder was then added to the alcohol/propylene glycol mixture. In a containment hood, finasteride was added to the solution and stirred until dissolved. The preparation was cooled to room temperature. Ethoxy diglycol and latanoprost were added to the cooled solution and stirred well, until in solution. The final solution was brought to volume with absolute ethyl alcohol.

The amounts used are set out in Table 1 below:

| Component | Function | Quantity per unit | % |
|---|---|---|---|
| Propylene glycol | Solvent | 30 ml | 50 |
| Minoxidil USP | Active | 3 g | 5 |
| Finasteride USP | Active | 0.06 g | 0.1 |
| Ethoxy diglycol reagent | Solvent | 3 ml | 5 |
| Latanoprost (10,000 mcg/ml) | Active | 1.8 ml | 0.03 |
| Absolute ethyl alcohol | Solvent | QS 60 ml | 39.87 |
| TOTAL | | 60 ml | 100% |

Various modifications for the preparation of the composition of the invention will be apparent to the skilled worker. Furthermore, other pharmaceutically acceptable additives such as suspending agents, emulsifying agents, non-aqueous vehicles and preservatives can be added. The techniques for the preparation of these compositions are well known in the art and reference may be had to Remington's Pharmaceutical Sciences, 18$^{th}$ edition, Mack Publishing Co., Easton, Pa., USA 18042.

Example 2

Preparation of Composition Comprising Minoxidil

A composition comprising 5% minoxidil was prepared. Absolute ethyl alcohol was mixed with propylene glycol and heated to 55° to 65° C. The minoxidil powder was added to the alcohol/propylene glycol mixture. Ethoxy diglycol was added and the solution was stirred. The final solution was brought to volume with absolute ethyl alcohol to obtain a solution comprising 5% minoxidil.

Example 3

Preparation of Composition Comprising Finasteride

A composition comprising 0.1% finasteride was also prepared. Absolute ethyl alcohol was mixed with propylene glycol. Finasteride was added to the alcohol/propylene glycol mixture to obtain a solution having a concentration of 0.1% finasteride. Absolute ethyl alcohol also serves the function of preservative.

Example 4

Preparation of Composition Comprising Latanoprost

A solution comprising 0.03% latanoprost was prepared. Absolute ethyl alcohol was mixed with propylene glycol. The latanoprost was added to the alcohol/propylene glycol mixture. The final solution was brought to volume with absolute ethyl alcohol in order to obtain a solution having a concentration of 0.03% latanoprost. The absolute ethyl alcohol also serves the function of preservative in this composition.

Example 5

Treatment of Participants with Composition of Invention and Comparators—Analysis and Measurements For each participant, the distance between the base of the nose and the middle of the hair crown was noted, as well as the distance separating the most distal part of the helix and the hair crown. A square area of two centimeters by two centimeters was measured around the middle point of the hair crown (marked by a washable felt crayon). Photographs were taken of each participant's scalp.

The participants were seen at monthly intervals over a six-month period and their hair was analysed in the manner described above and photographs taken.

Results

A. Treatment with Composition Comprising Finasteride, Latanoprost and Minoxidil

Each participant first had his hair analysed as described above and photographs taken. Following the first analysis, each participant was provided with a solution comprising 0.1% finasteride, 0.03% latanoprost and 5% minoxidil prepared as described in Example 1 above. The participants applied 1 ml to the scalp, once a day after cleansing. The 1 ml was applied as 10 metered dose sprays of 0.1 ml.

Figure 1B:
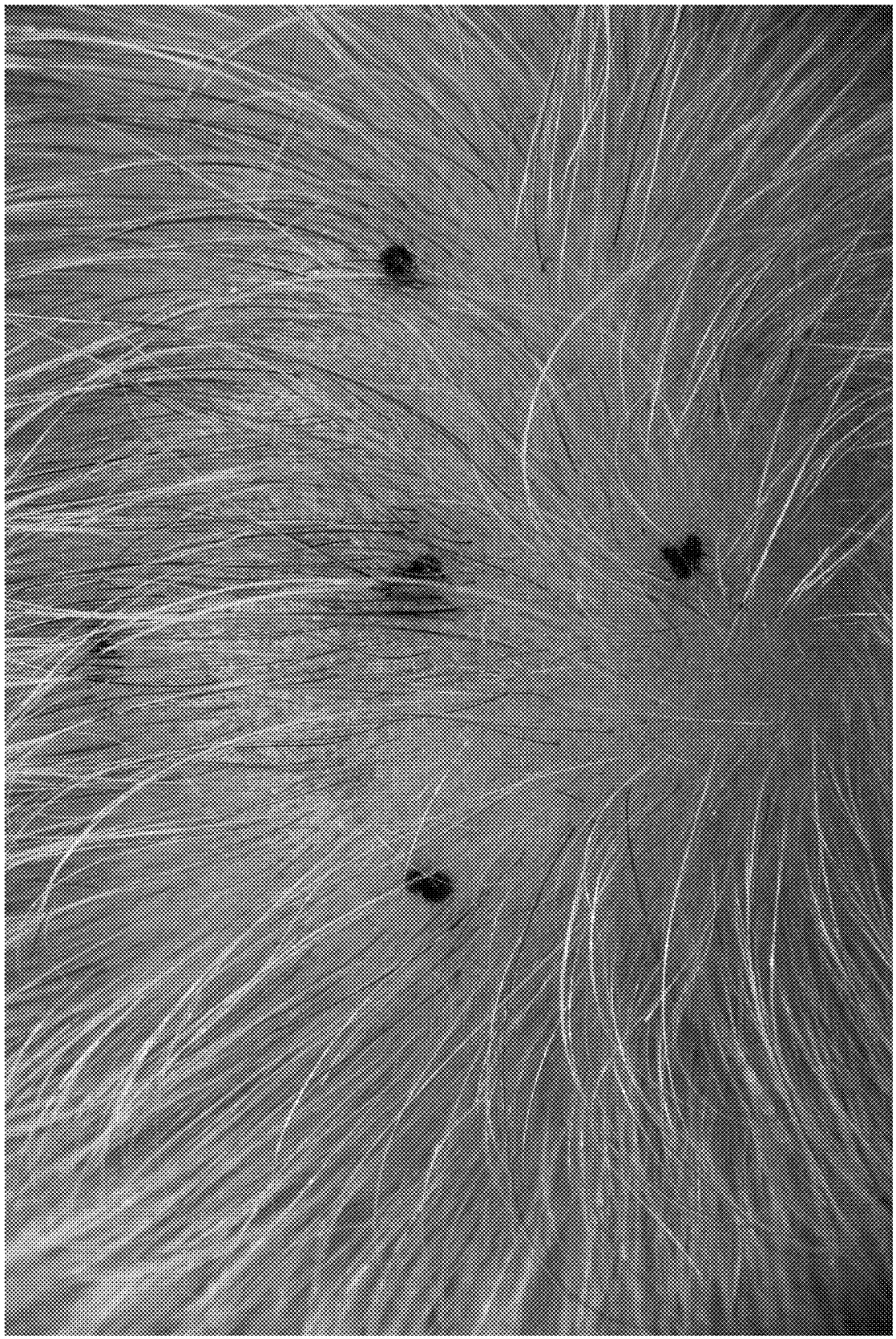
Figure 1C:
Figure 1D:
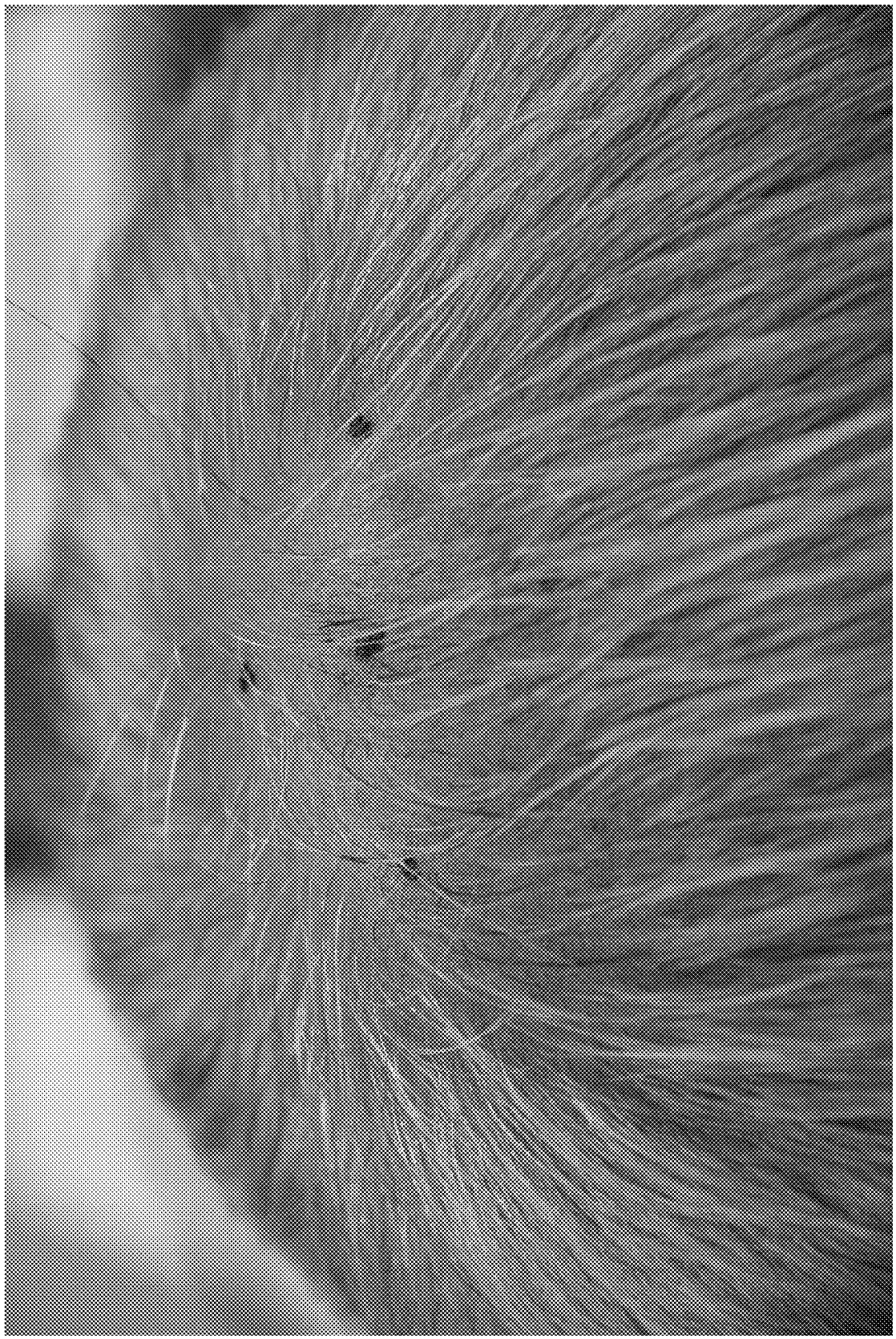
Figure 1E:
Figure 1F:
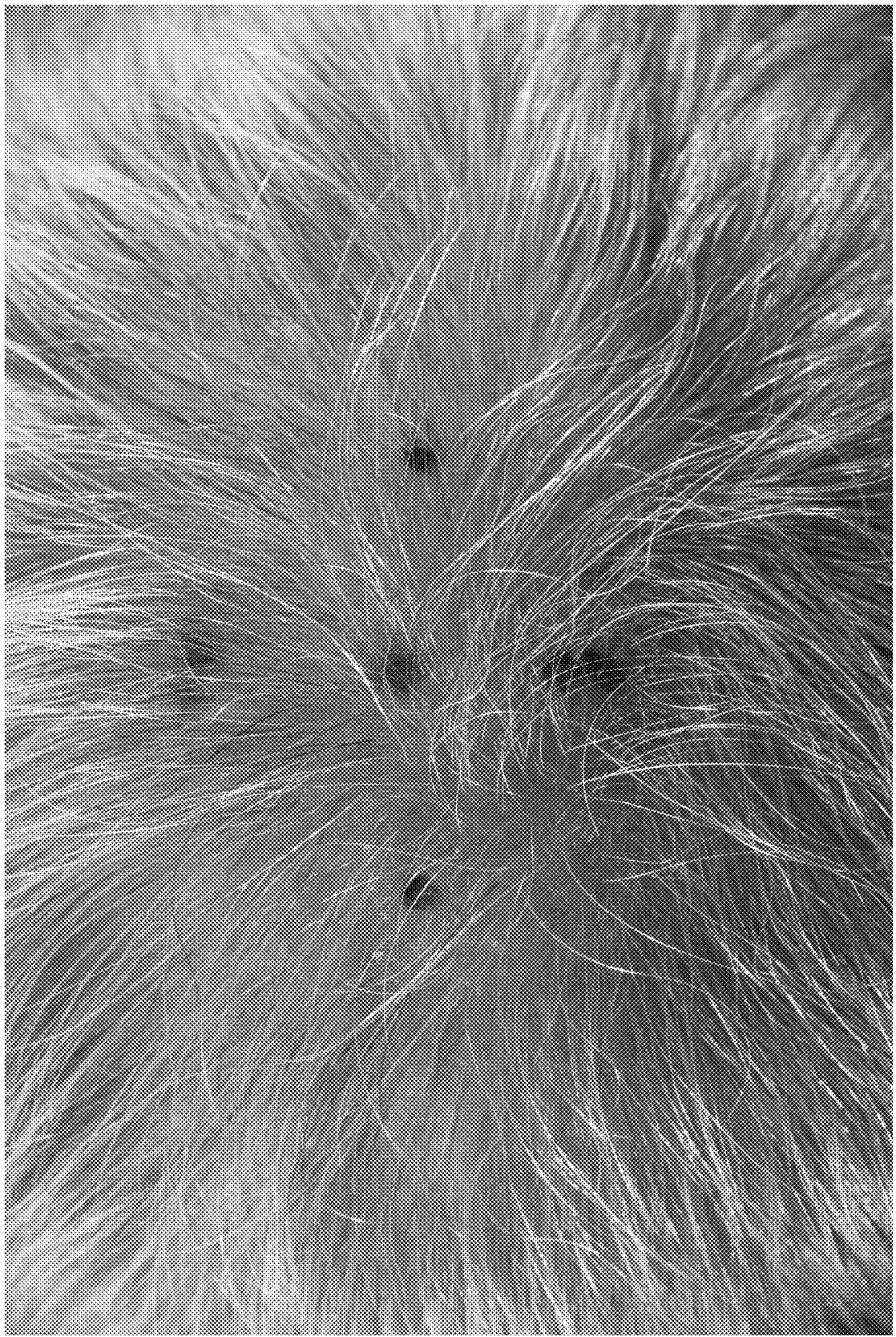
Figure 1G:
Figure 1H:
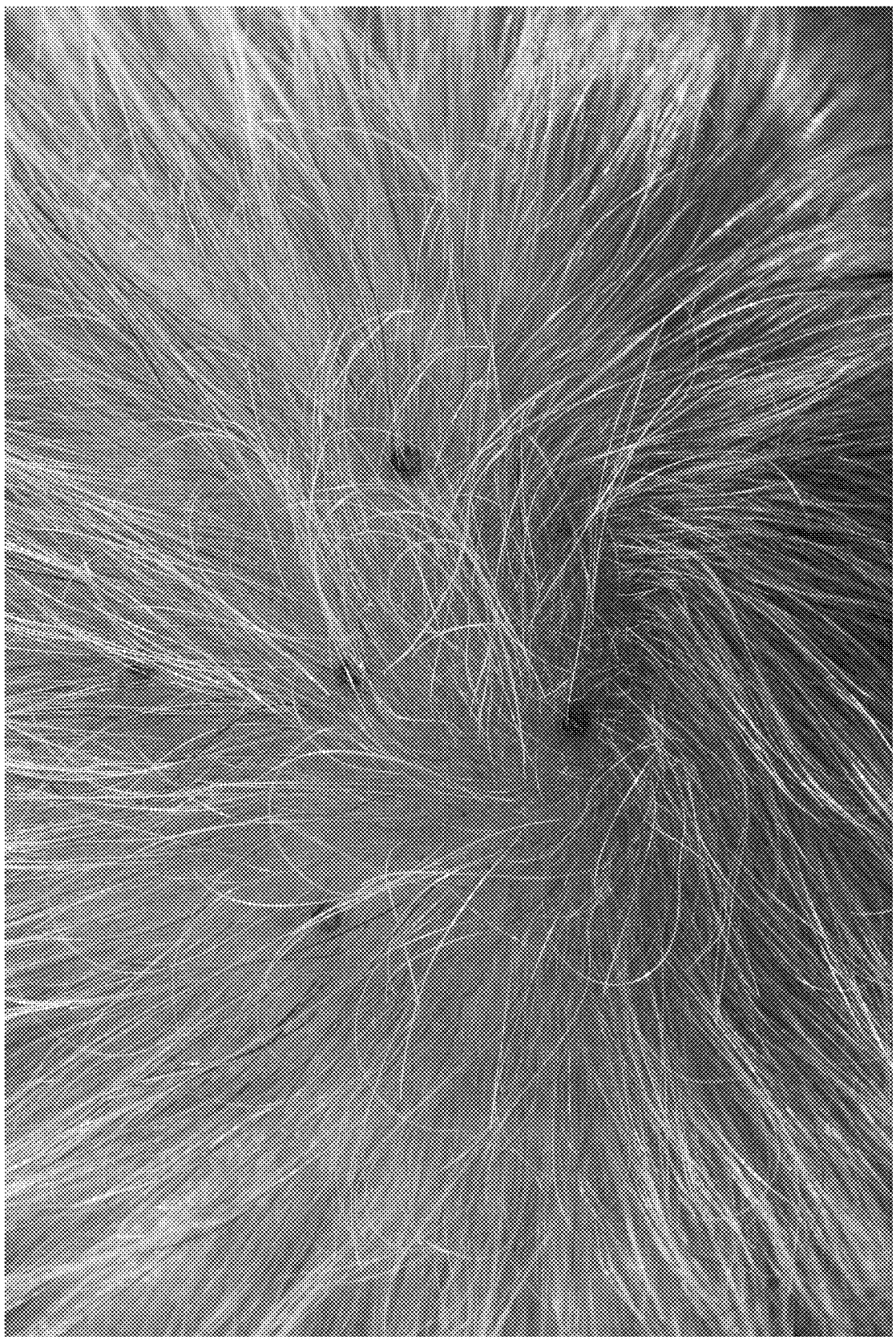
Figure 1I:
Figure 1J:
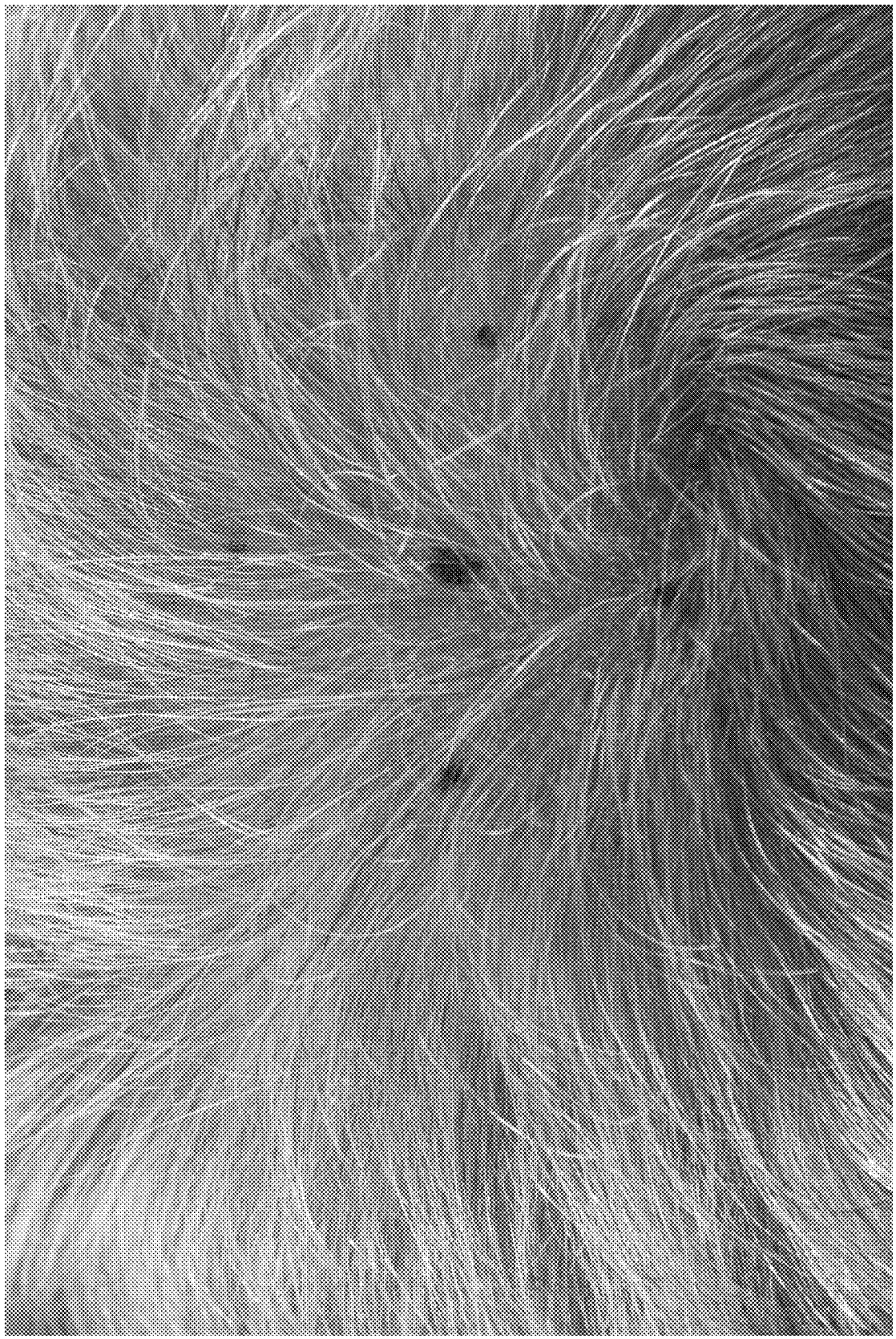
Figure 1K:
Figure 1L:
Figure 2A:
FIGS. 2A to 2L are a series of photographs showing the scalp of participant 2 prior to treatment and at intervals throughout the course of a six month treatment with a composition of the invention.
Figure 2B:
Figure 2C:
Figure 2D:
Figure 2E:
Figure 2F:
Figure 2G:
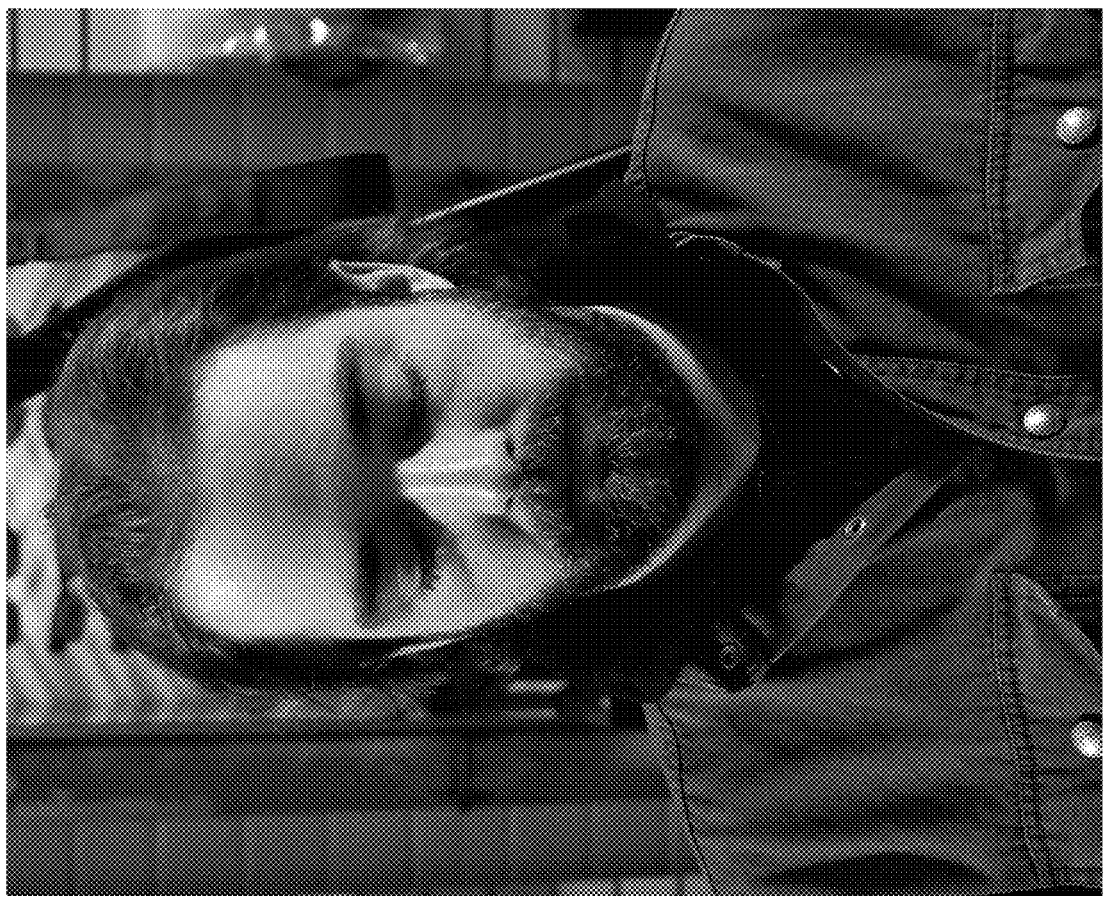
Figure 2H:
Figure 2I:
Figure 2J:
Figure 2K:
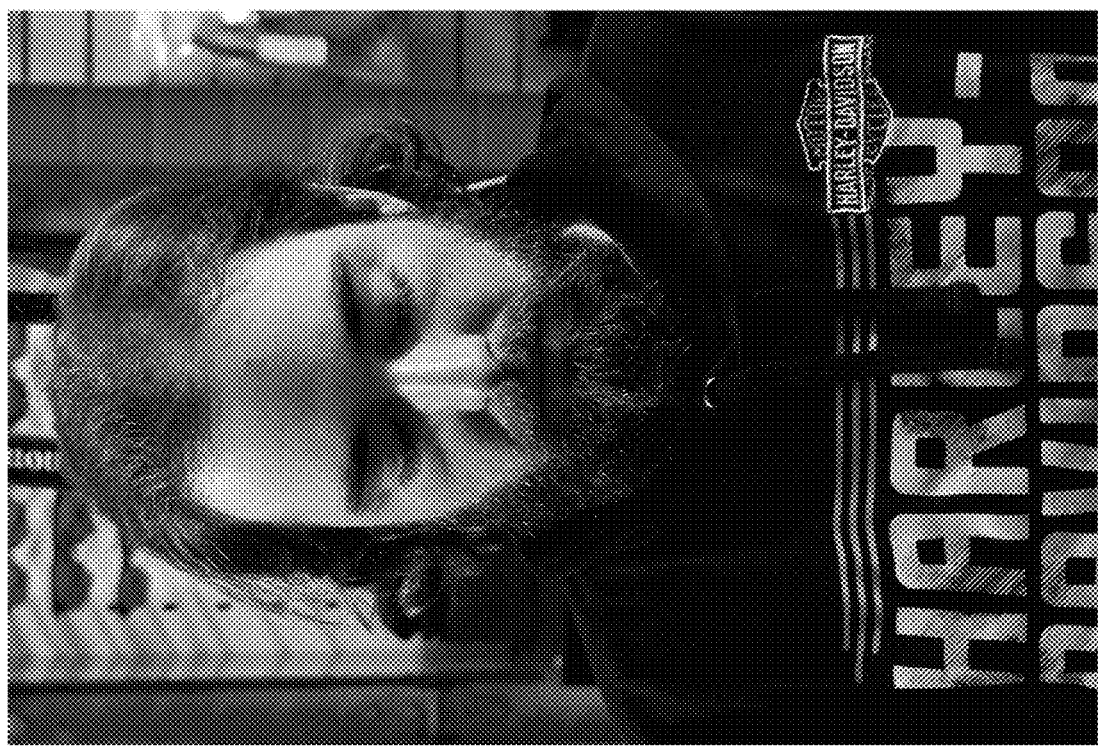
Figure 2L:
Figure 3A:
FIGS. 3A to 3L are a series of photographs showing the scalp of participant 3 prior to treatment and at intervals throughout the course of a six month treatment with a composition of the invention.
Figure 3B:
Figure 3C:
Figure 3D:
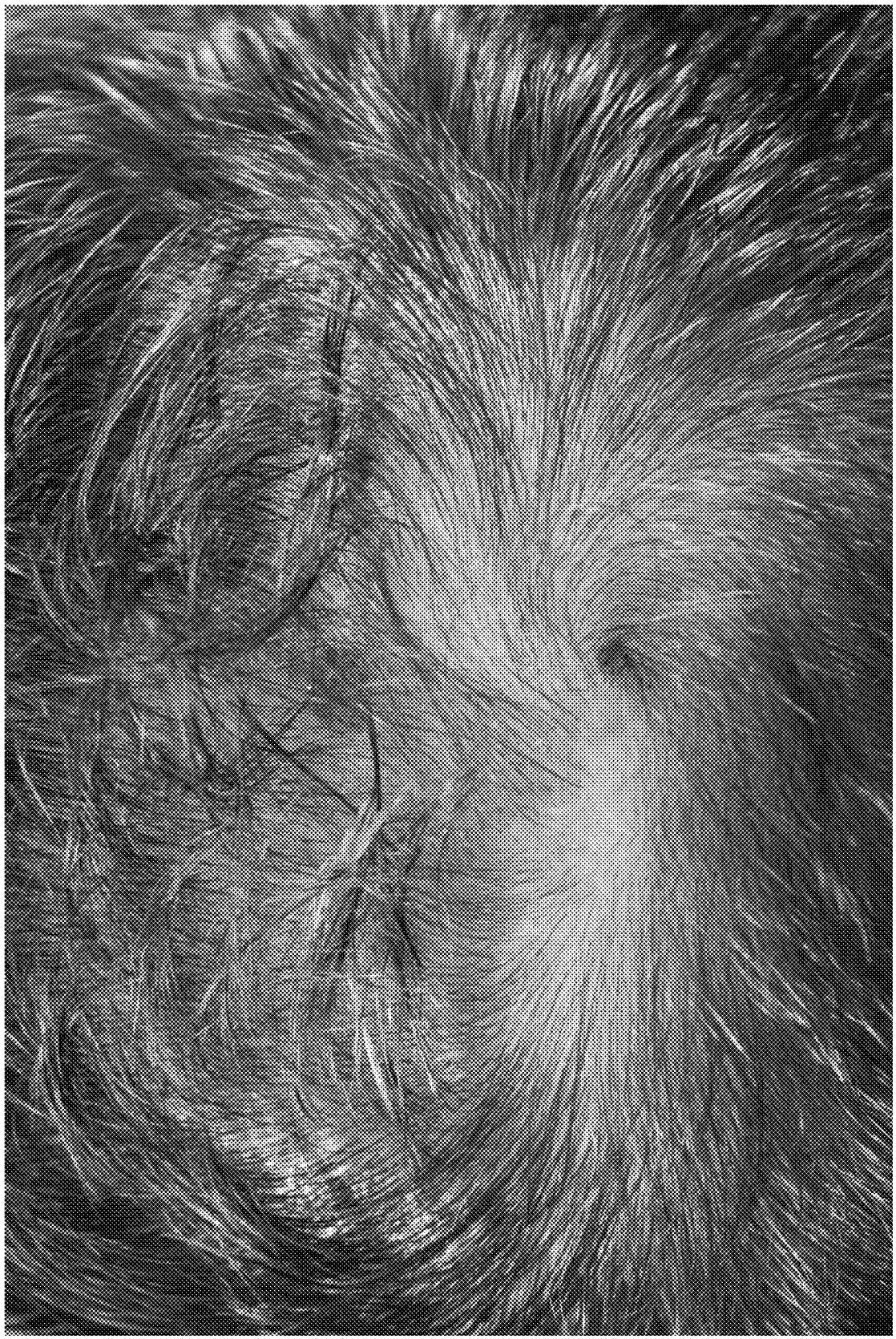
Figure 3E:
Figure 3F:
Figure 3G:
Figure 3H:
Figure 3I:
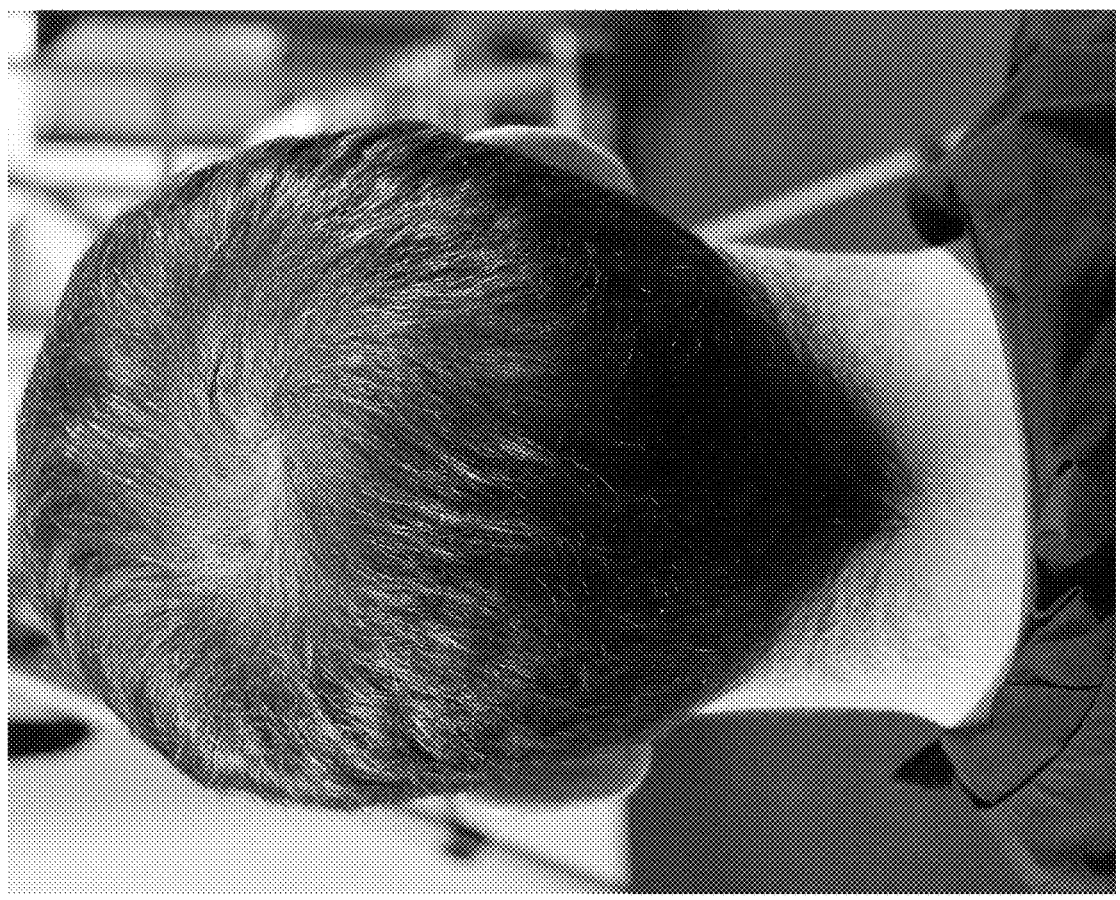
Figure 3J:
Figure 3K:
Figure 3L:
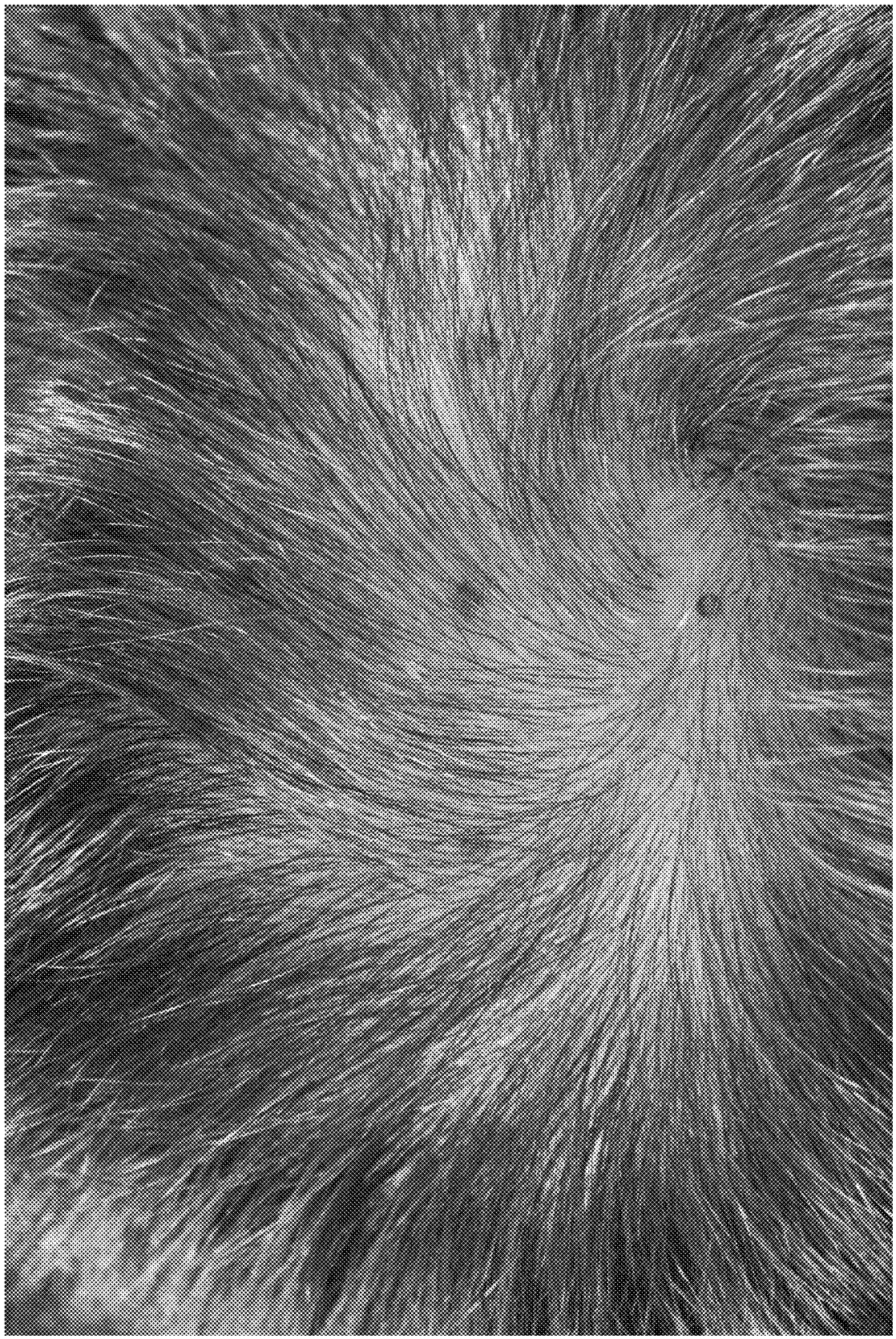

The results for three participants are provided. Participant 1 was a male of 61 years of age (FIG. 1). Participant 2 was a male of 23 years of age (FIG. 2) while participant 3 was a male of 29 years of age (FIG. 3). All three participants had androgenetic alopecia, as did the participants of the comparator groups.

FIGS. 1, 2 and 3 clearly show a marked decrease of hair loss and an increase in hair regrowth in all three participants.

B. Comparison with Treatment with Minoxidil, Finasteride and Latanoprost Alone

Each participant first had his hair analysed as described in part A above and photographs taken. Following the first analysis, each participant was provided with a solution comprising either 5% minoxidil, 0.1% finasteride, or 0.03% latanoprost. The compositions were prepared as described in Examples 2 to 4 above. The participants applied 1 ml to the scalp, once a day after cleansing. The 1 ml was applied as 10 metered dose sprays of 0.1 ml.

The results for the participants of each group are provided.

Figure 4A:
FIGS. 4A to 4L are a series of photographs showing the scalp of participant 4 prior to treatment and at intervals throughout the course of a six month treatment with a solution of 5% minoxidil only.
Figure 4B:
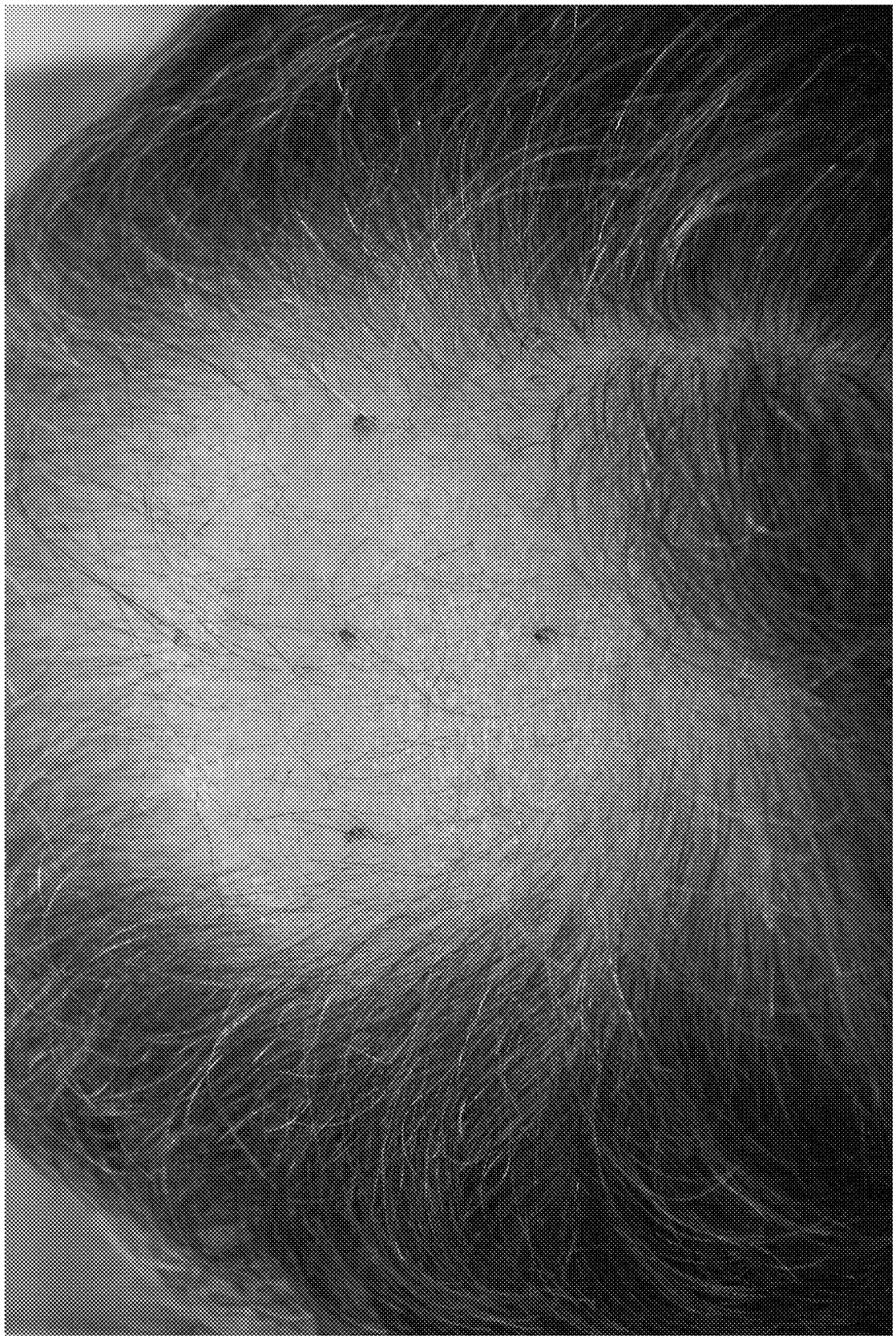
Figure 4C:
Figure 4D:
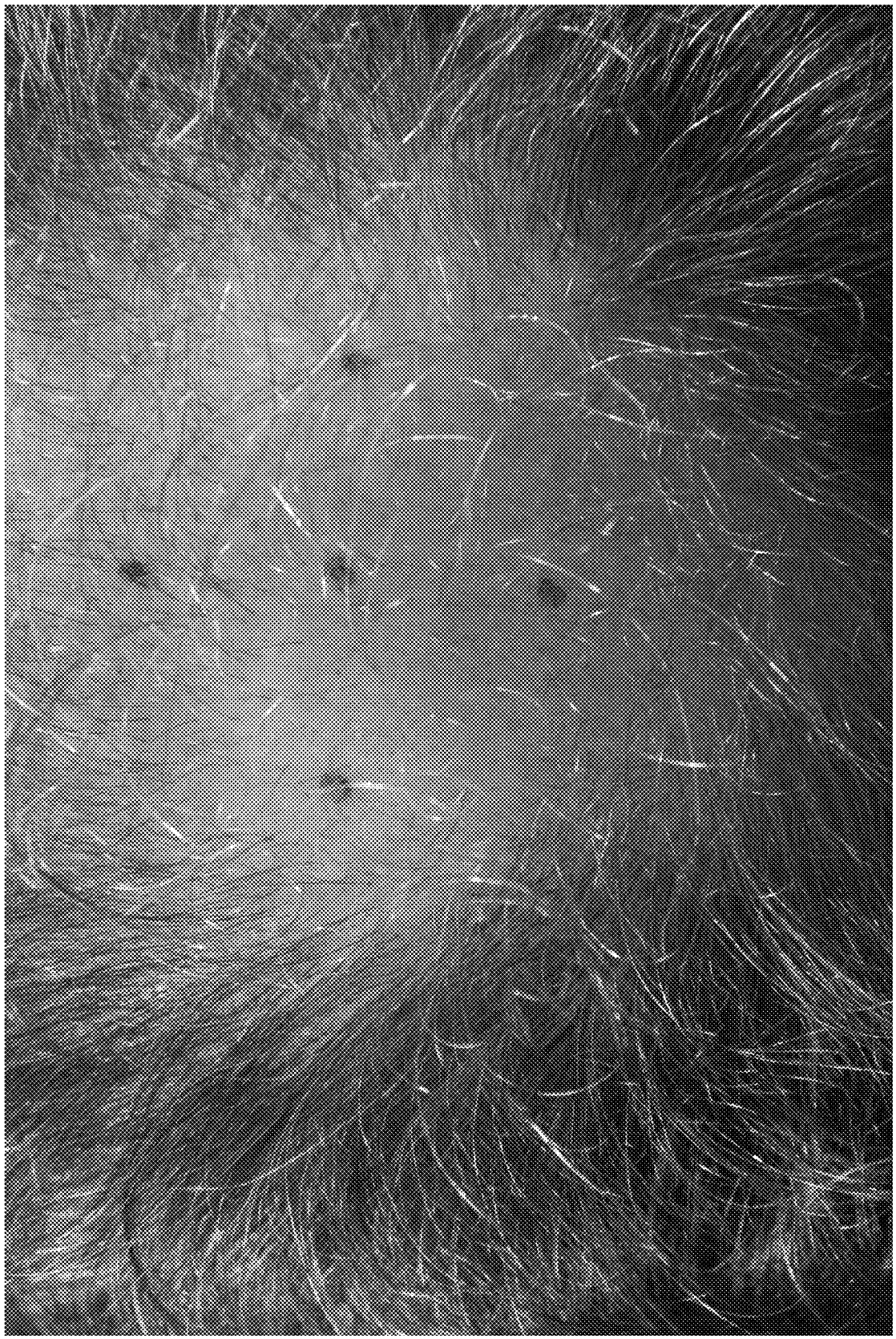
Figure 4E:
Figure 4F:
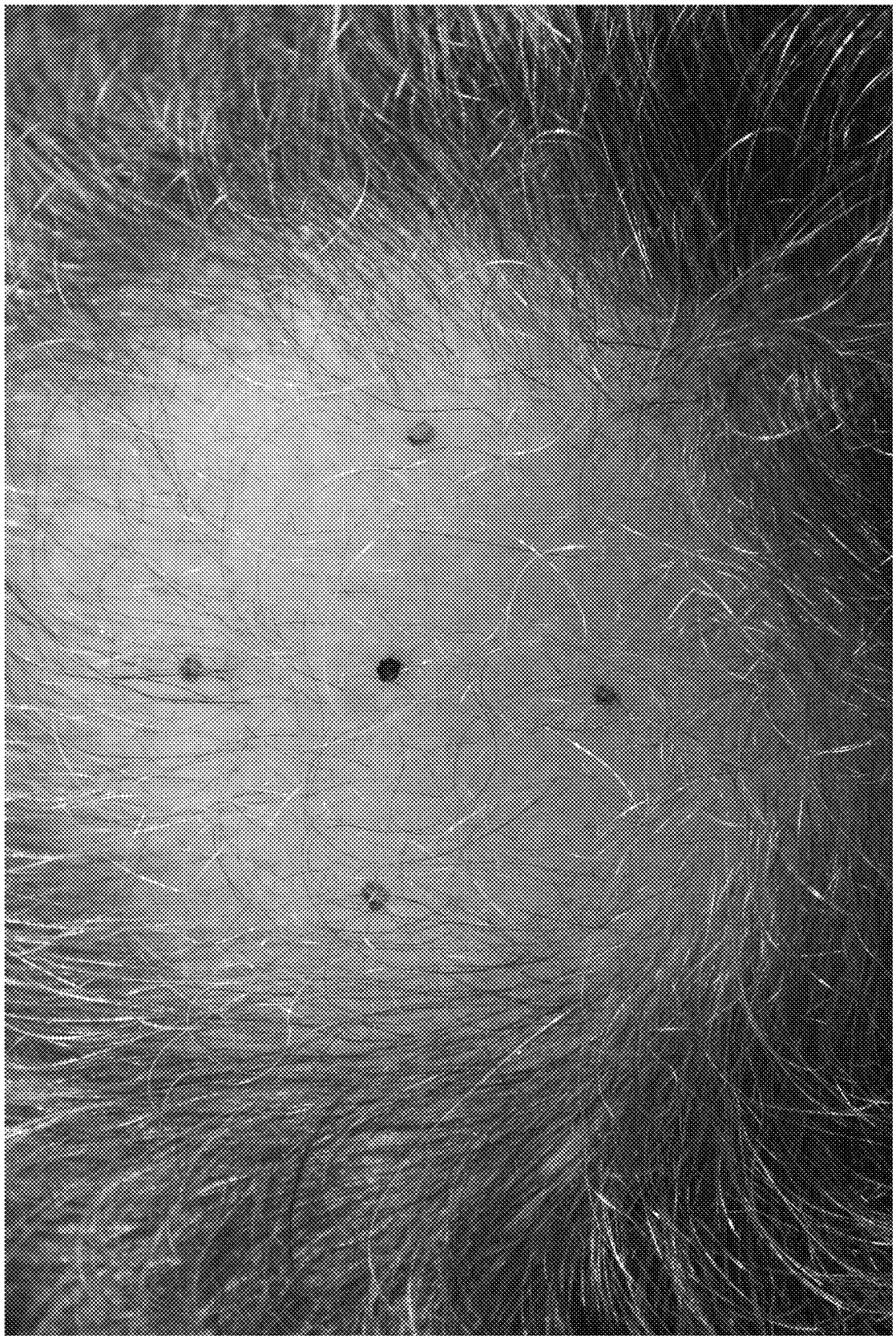
Figure 4G:
Figure 4H:
Figure 4I:
Figure 4J:
Figure 4K:
Figure 4L:
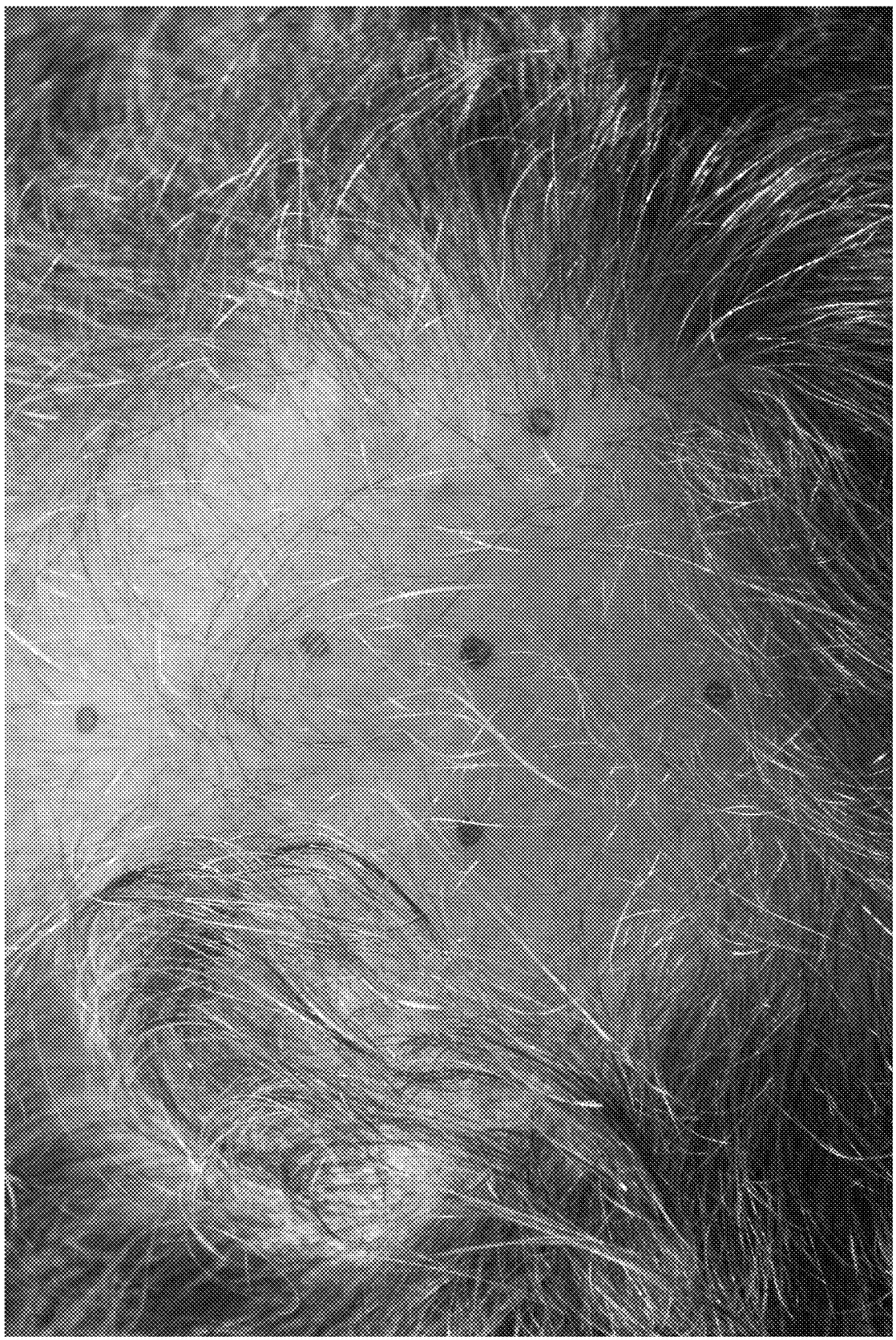

The participant for the minoxidil group was a 64 year old male. FIG. 4 shows the results obtained for this participant. Only a slight improvement in hair regrowth is observed and the results are very inferior to those seen with the composition of the invention.

Figure 5A:
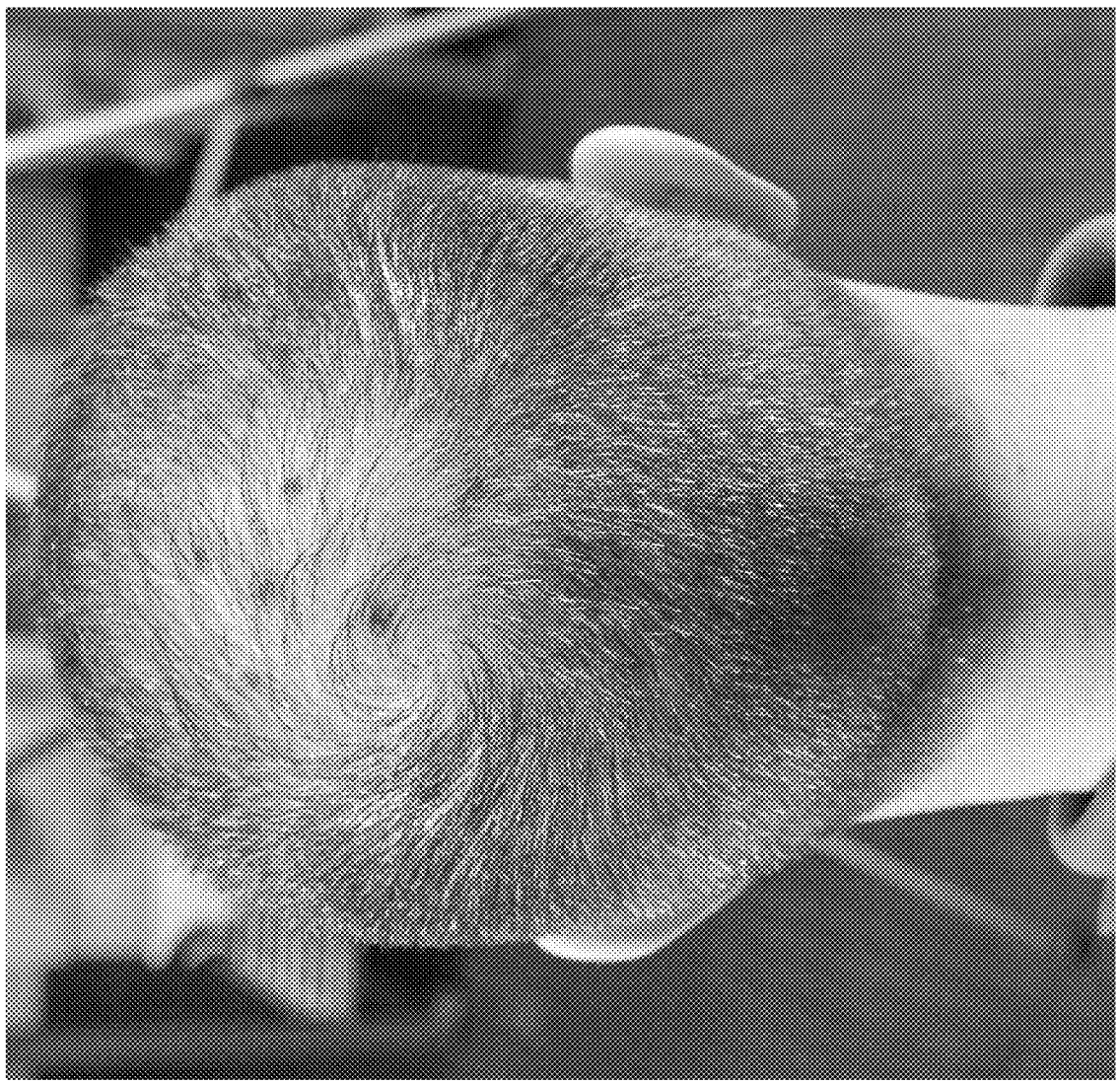
FIGS. 5A to 5L are a series of photographs showing the scalp of participant 5 prior to treatment and at intervals throughout the course of a six month treatment with a solution of 0.1% finasteride only.
Figure 5B:
Figure 5C:
Figure 5D:
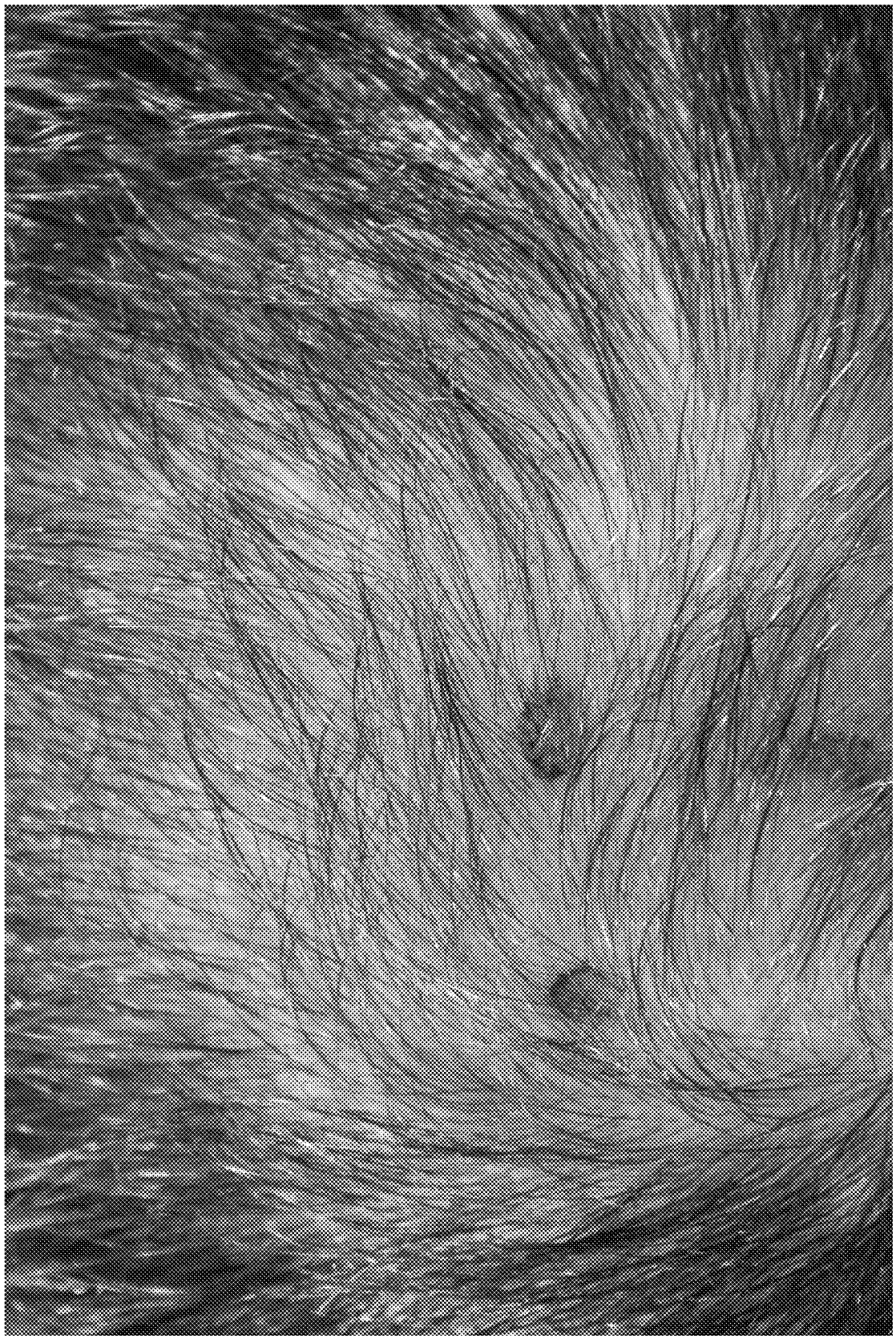
Figure 5E:
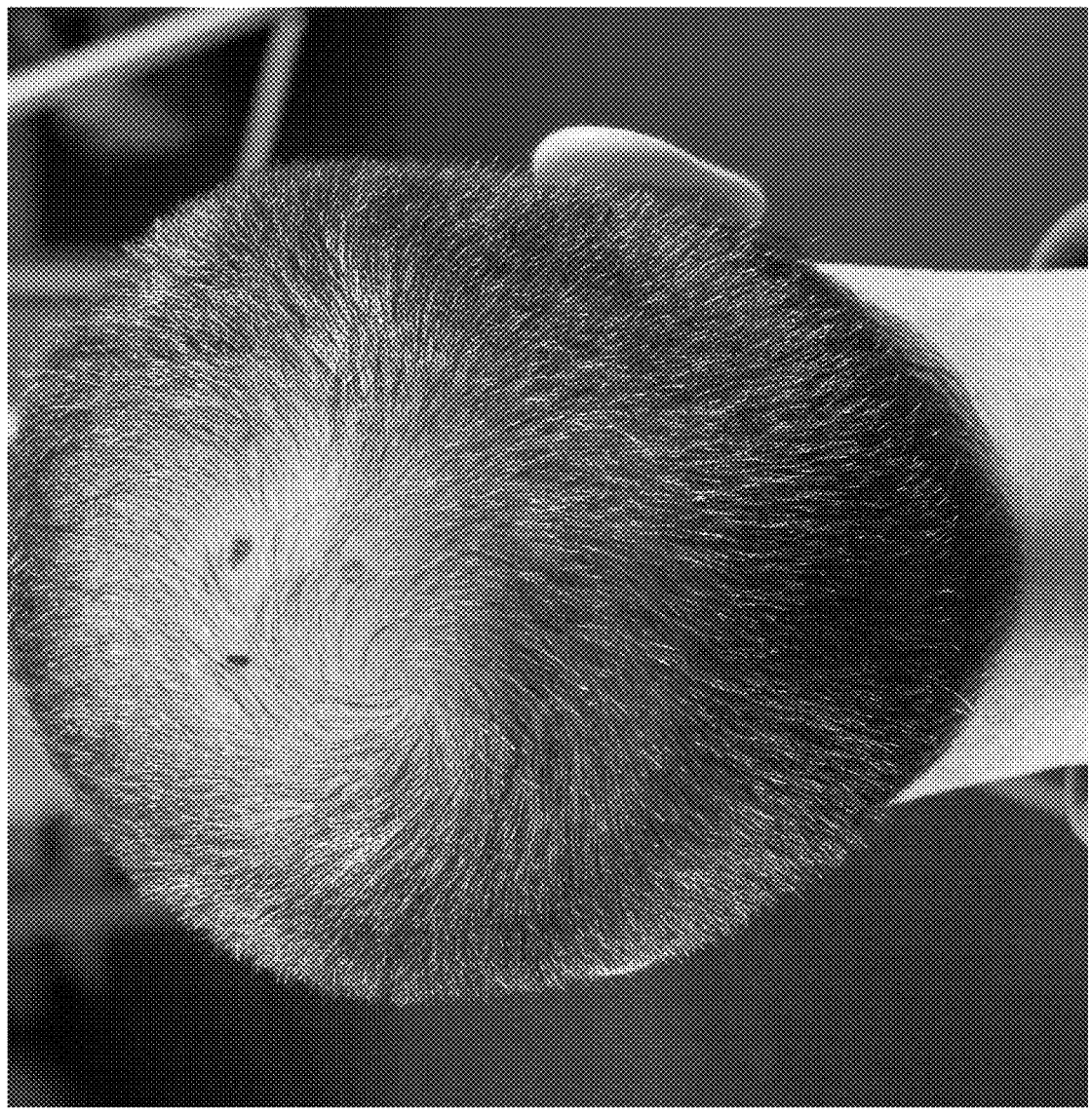
Figure 5F:
Figure 5G:
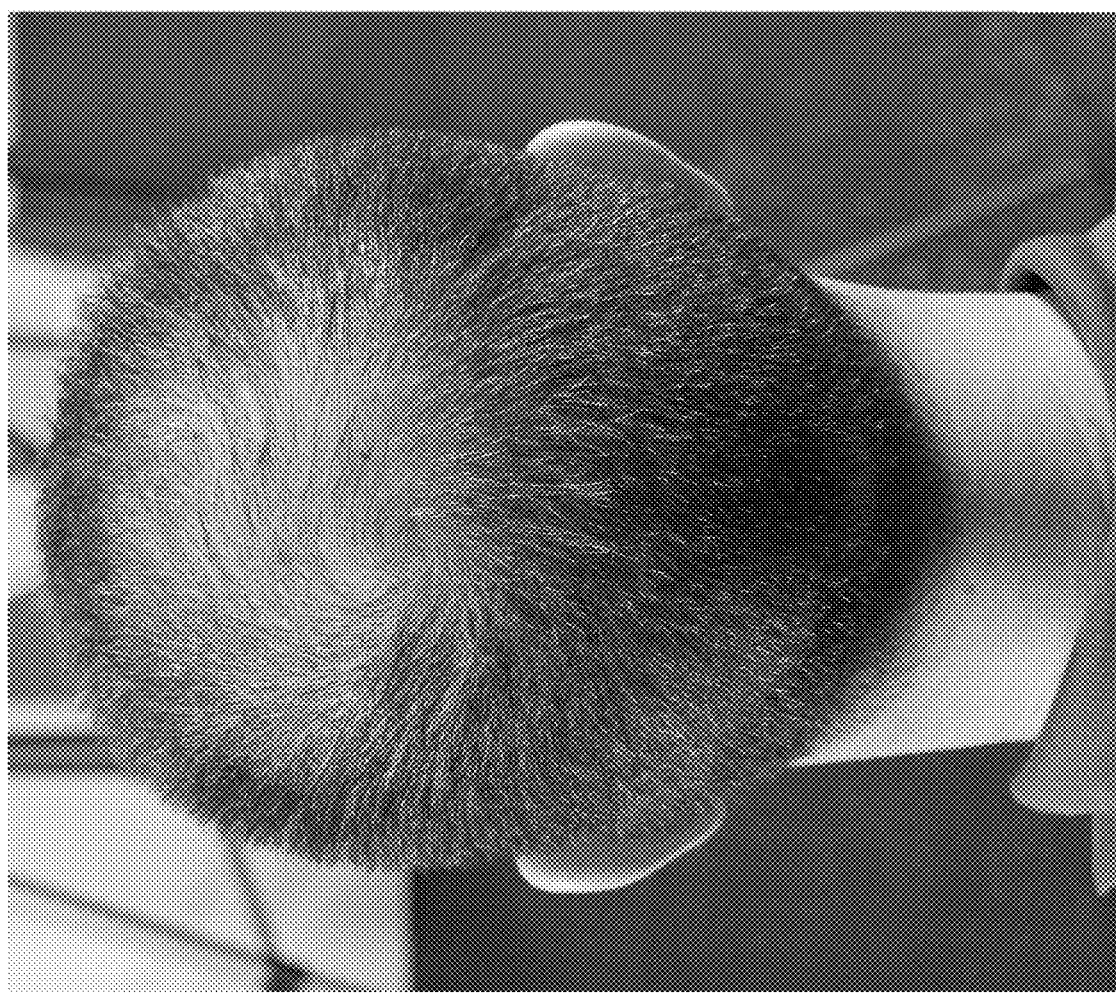
Figure 5H:
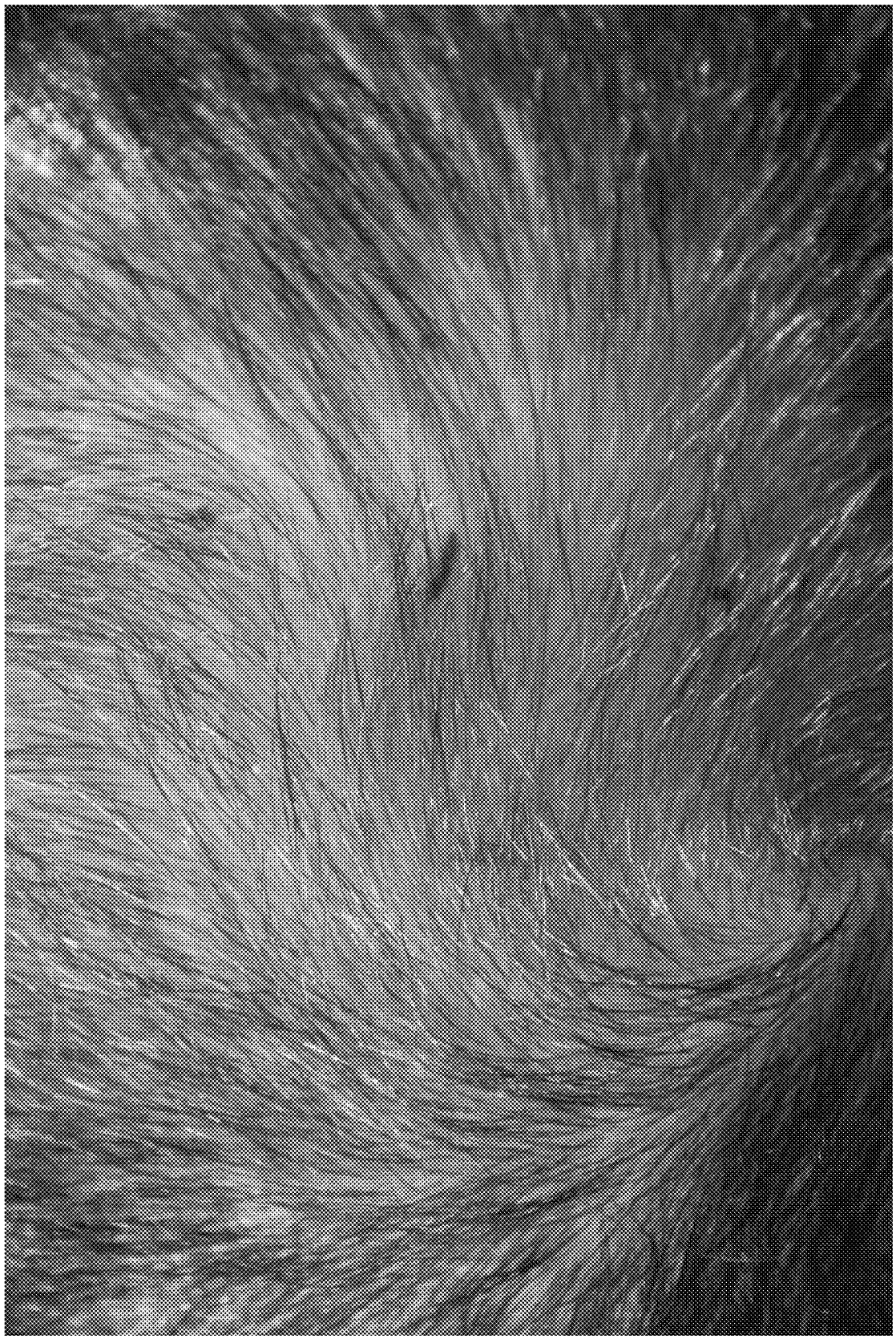
Figure 5I:
Figure 5J:
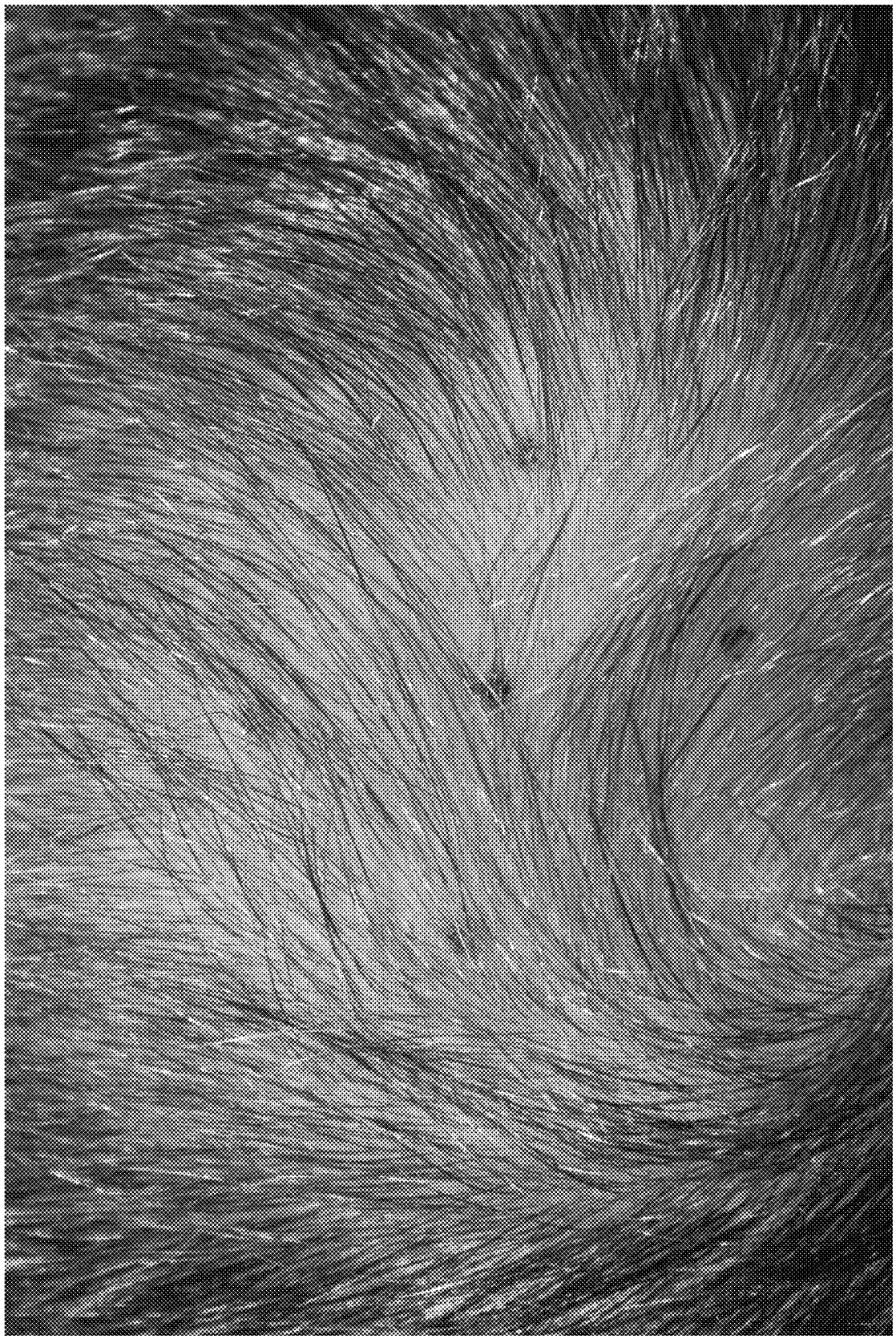
Figure 5K:
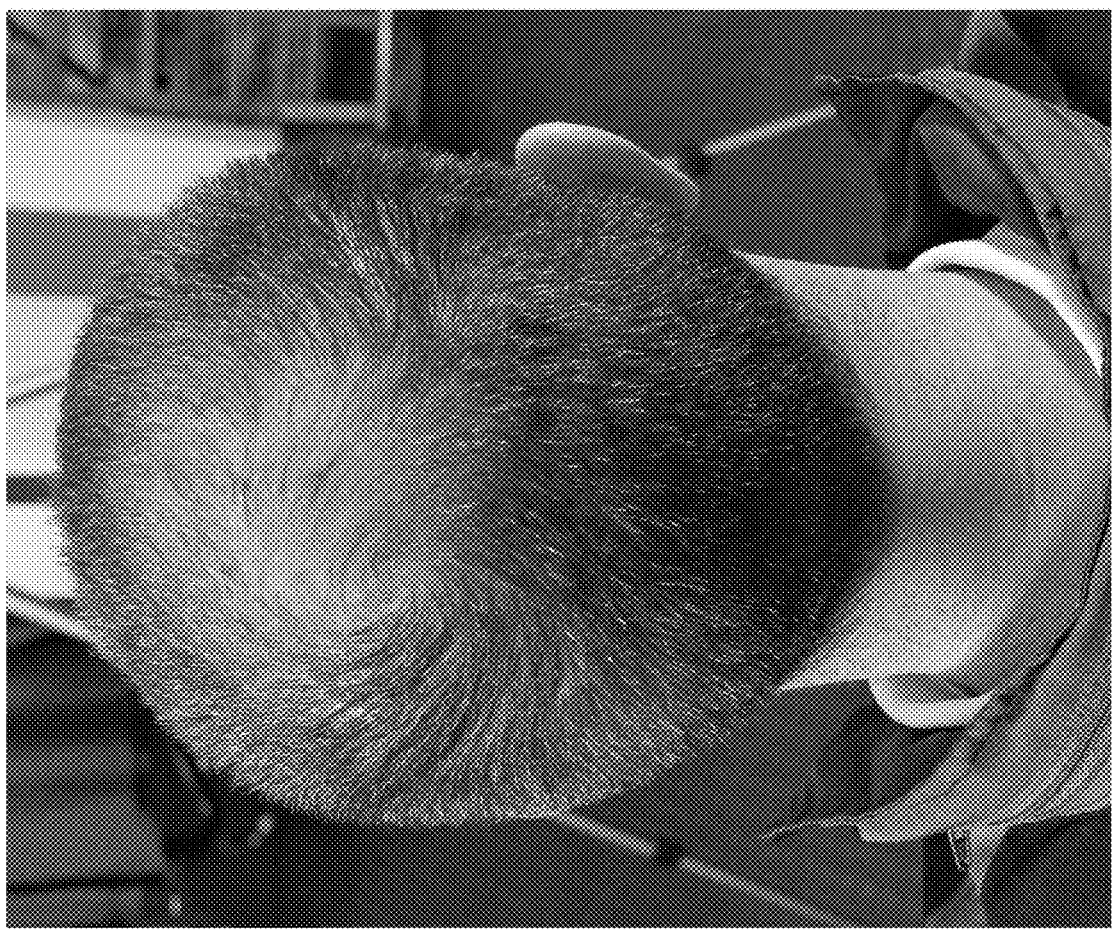
Figure 5L:
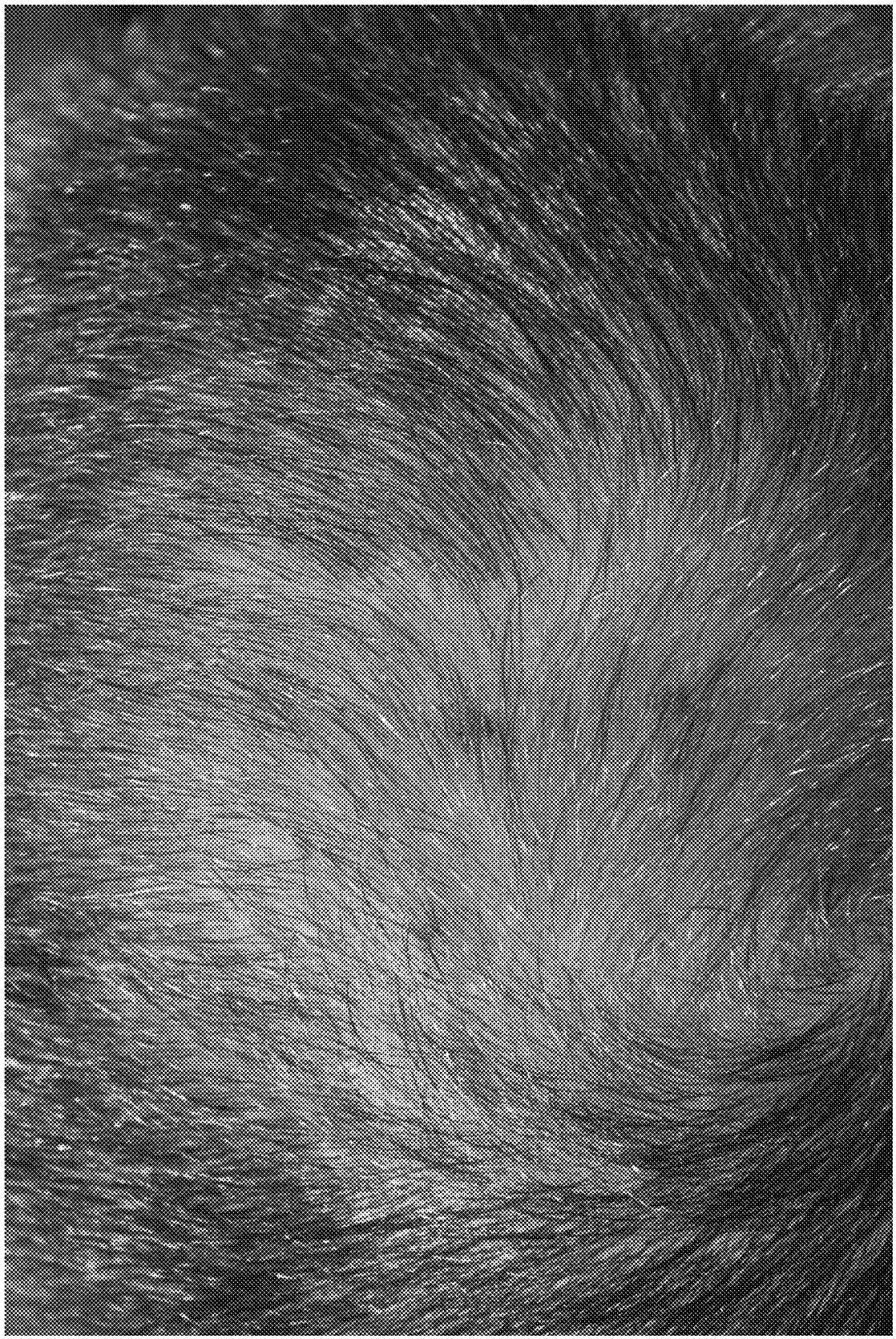
Figure 6A:
FIGS. 6A to 6L are a series of photographs showing the scalp of participant 6 prior to treatment and at intervals throughout the course of a six month treatment with a solution of 0.1% finasteride only.
Figure 6B:
Figure 6C:
Figure 6D:
Figure 6E:
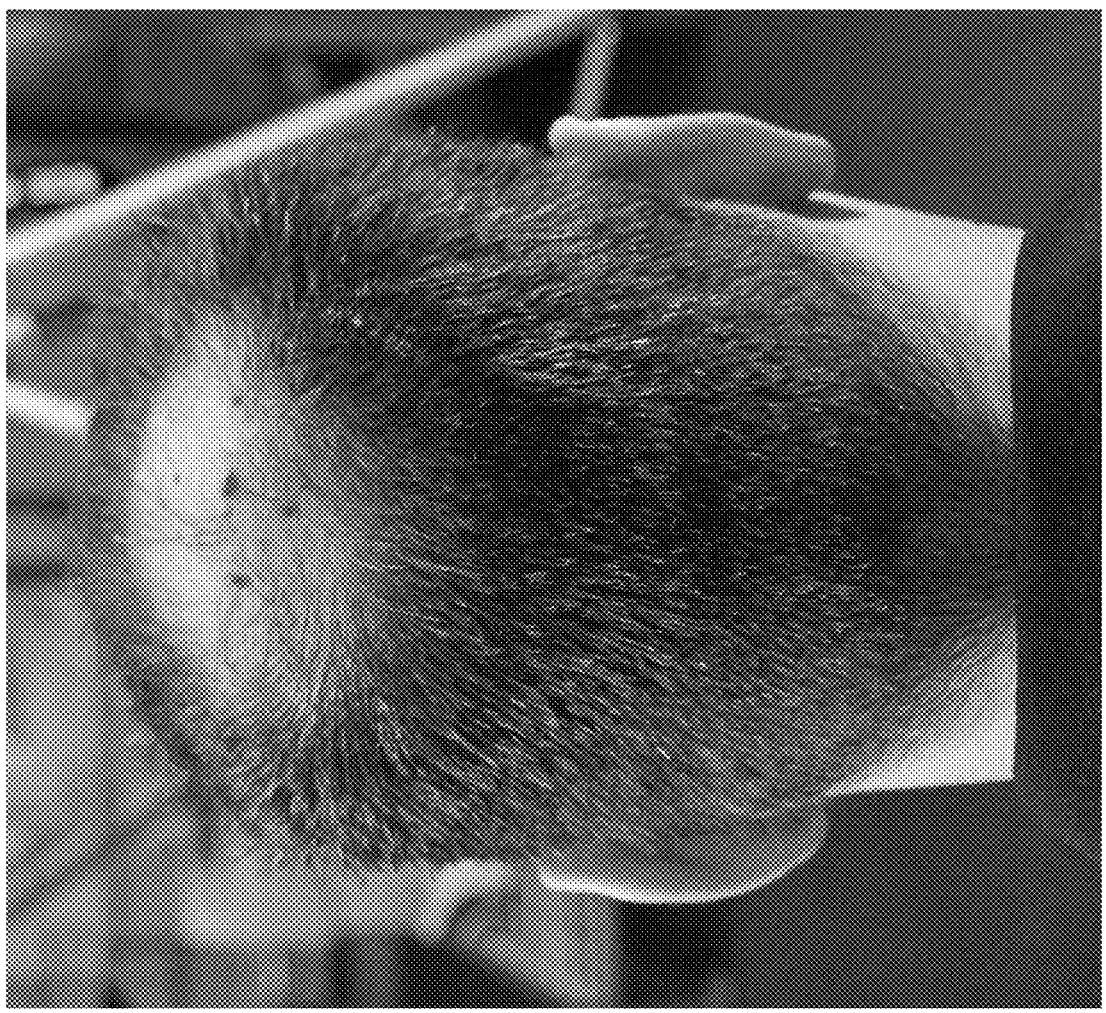
Figure 6F:
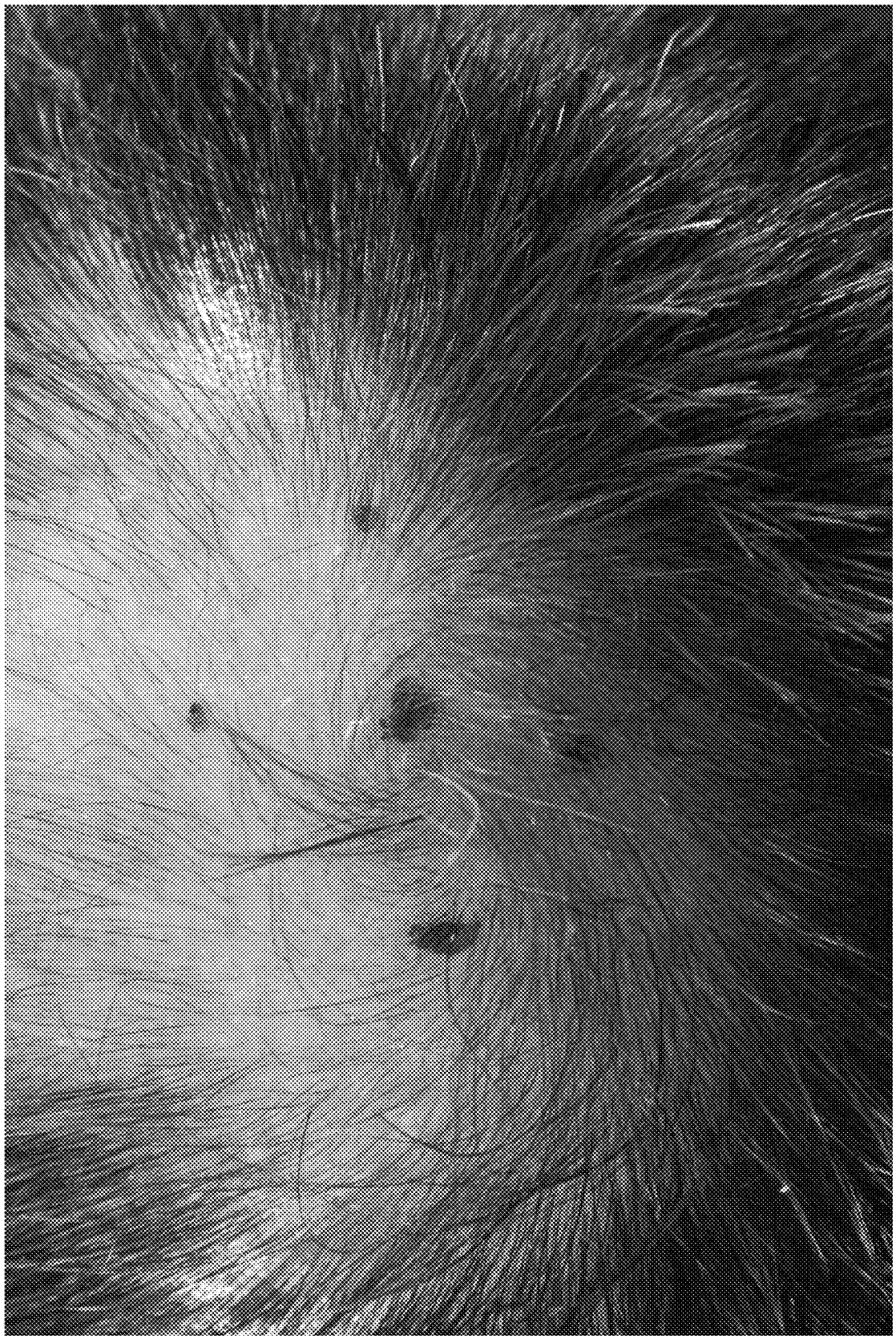
Figure 6G:
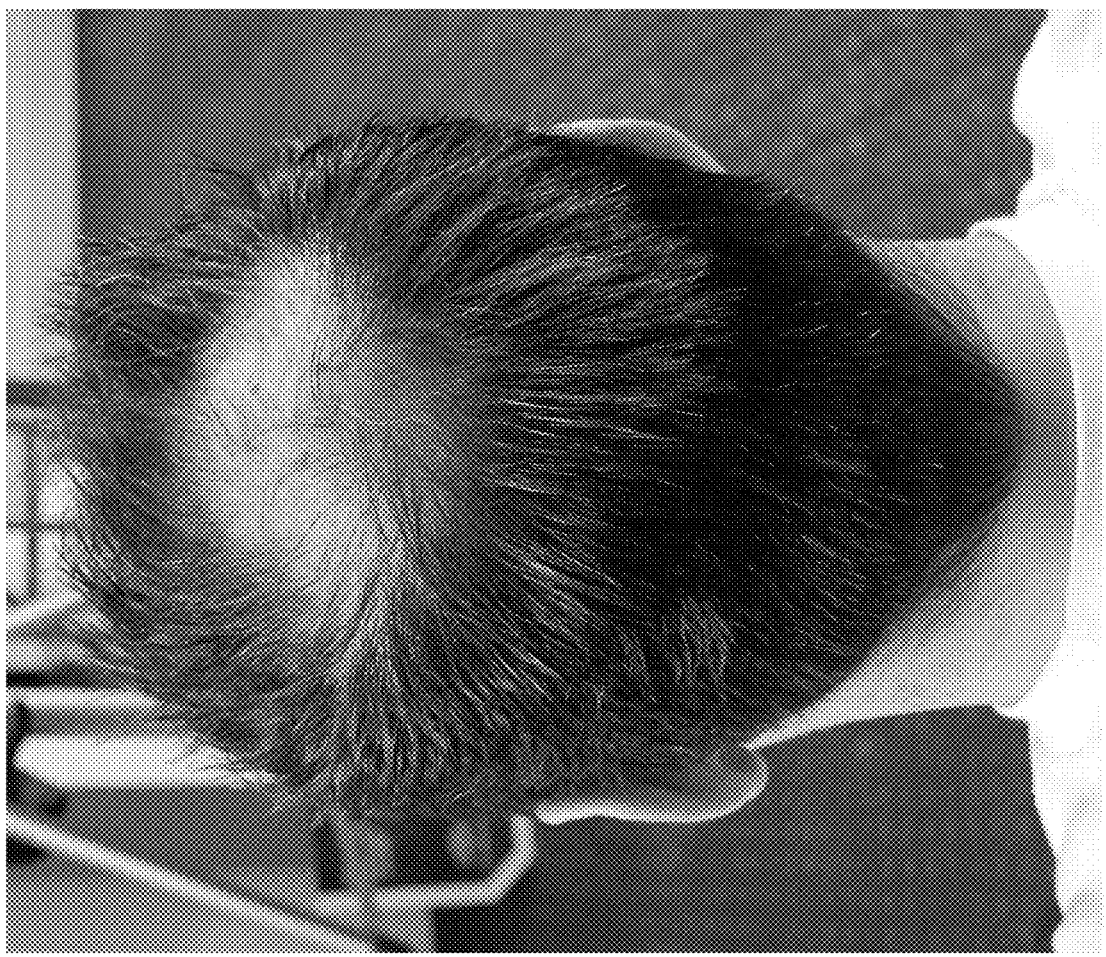
Figure 6H:
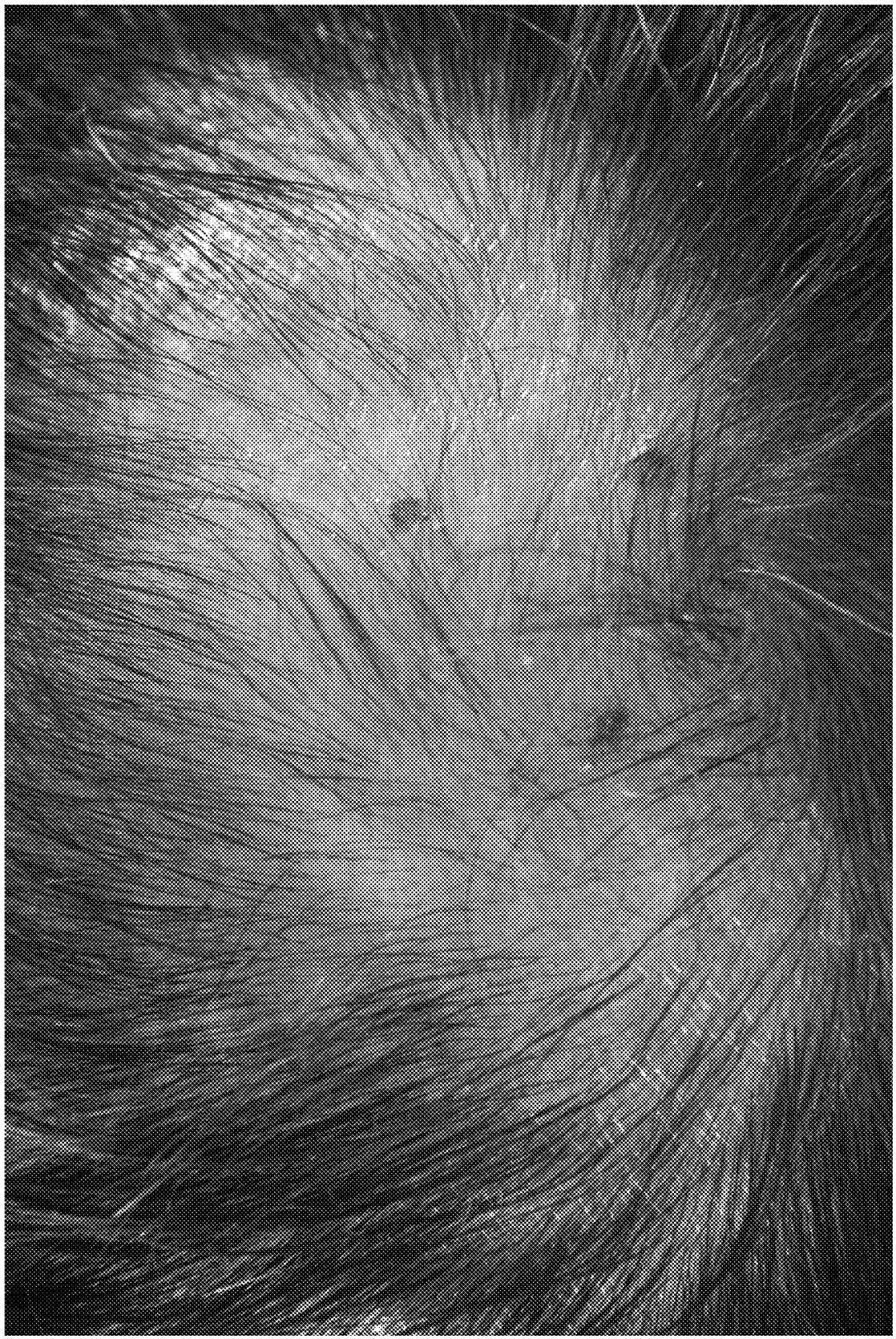
Figure 6I:
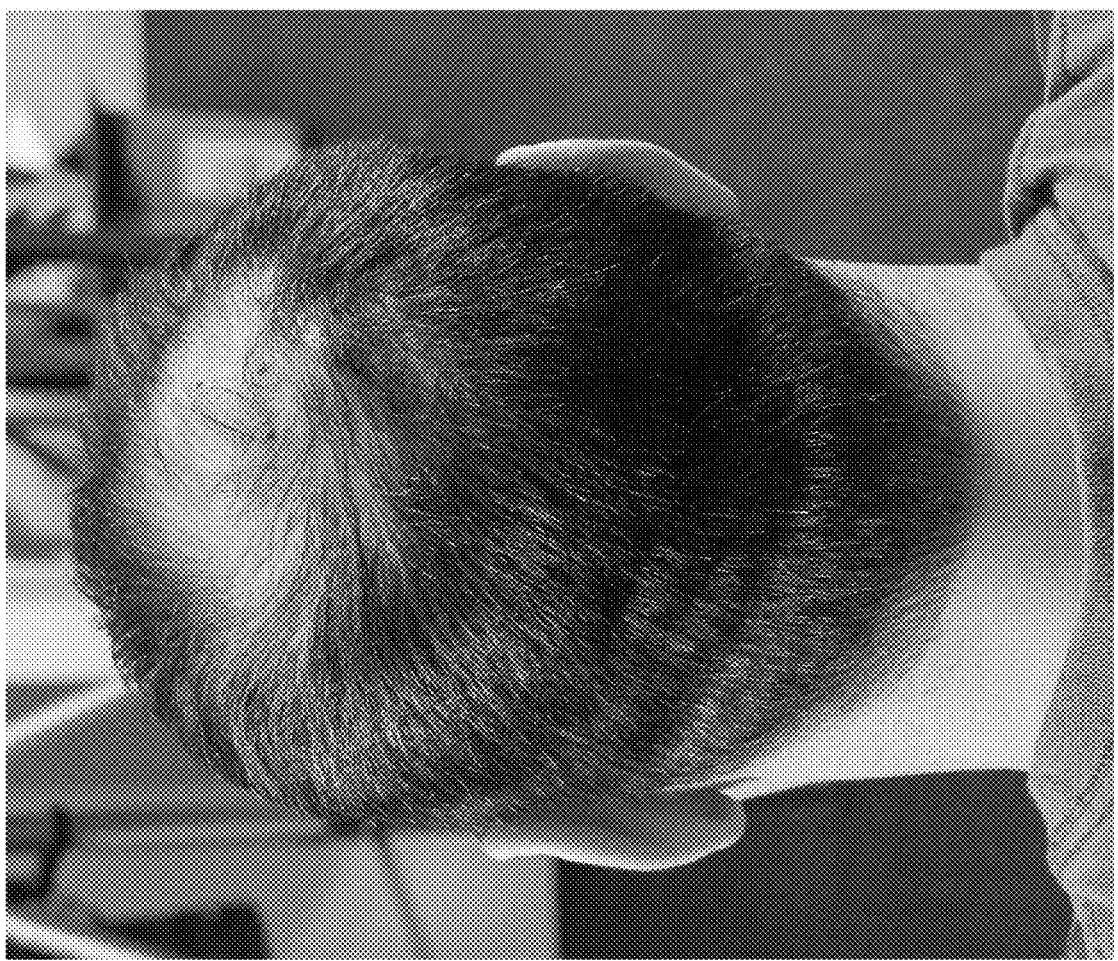
Figure 6J:
Figure 6K:
Figure 6L:
Figure 7A:
FIGS. 7A to 7G are a series of photographs showing the scalp of participant 7 prior to treatment and at intervals throughout the course of a six month treatment with a solution of 0.1% finasteride only.
Figure 7B:
Figure 7C:
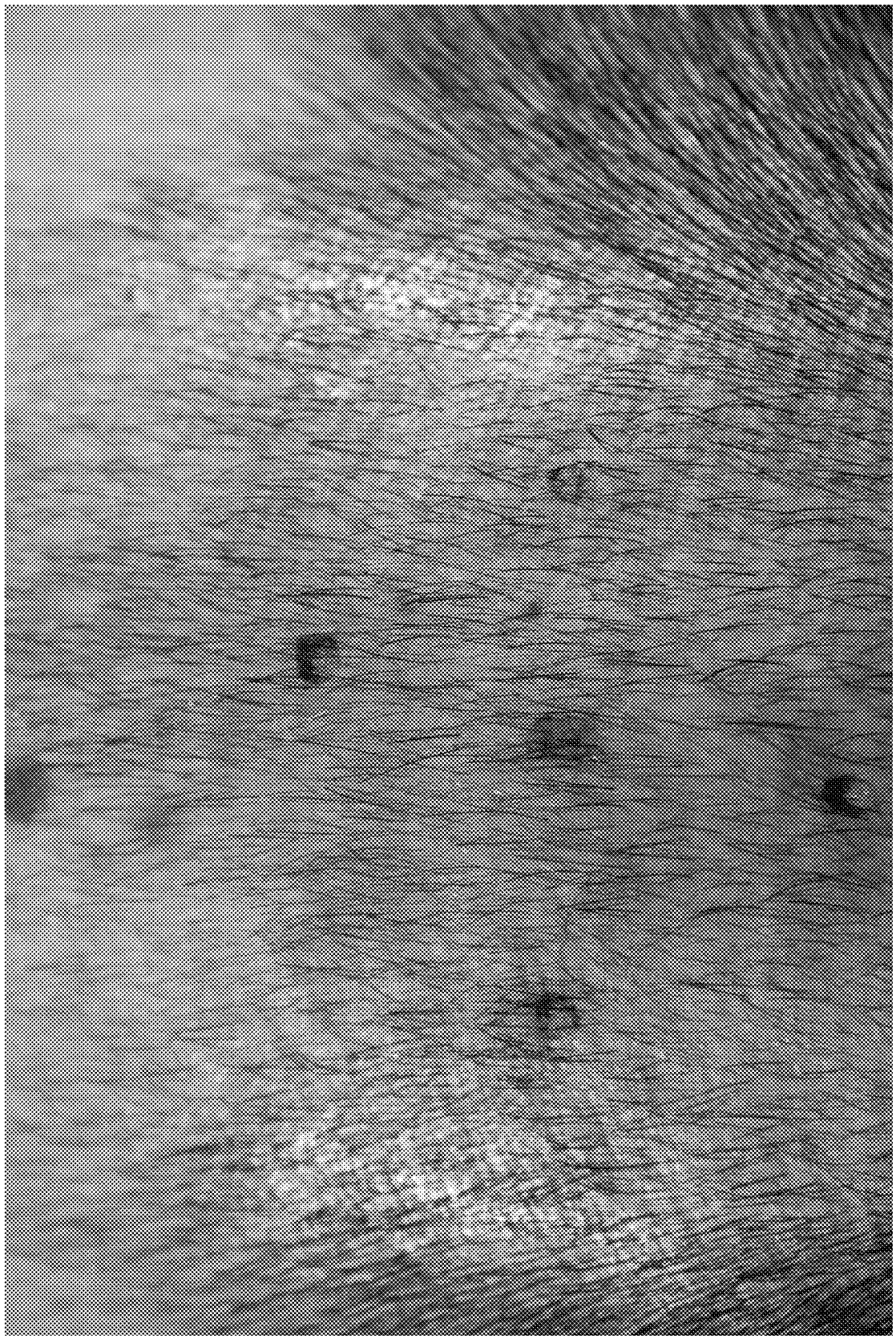
Figure 7D:
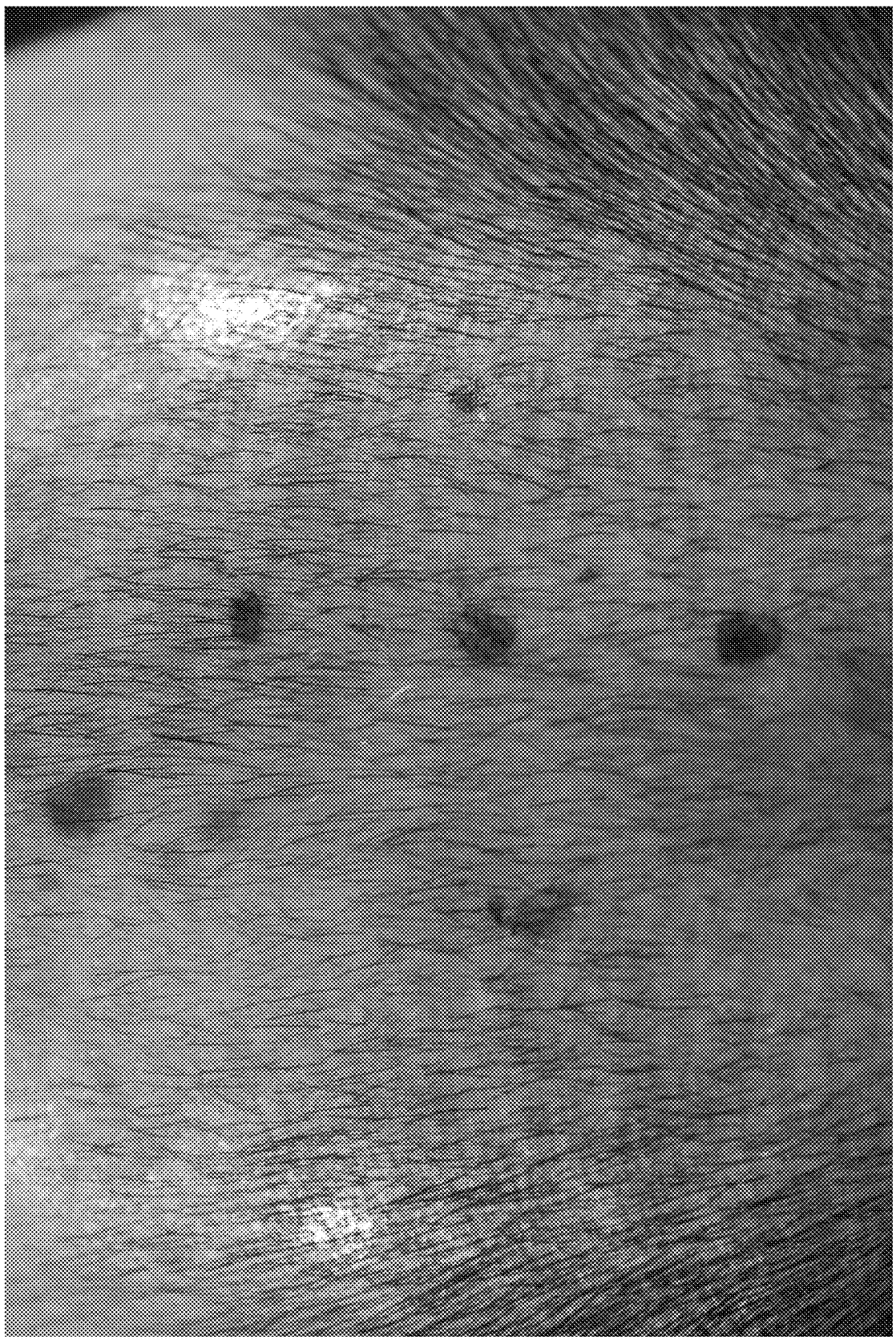
Figure 7E:
Figure 7F:
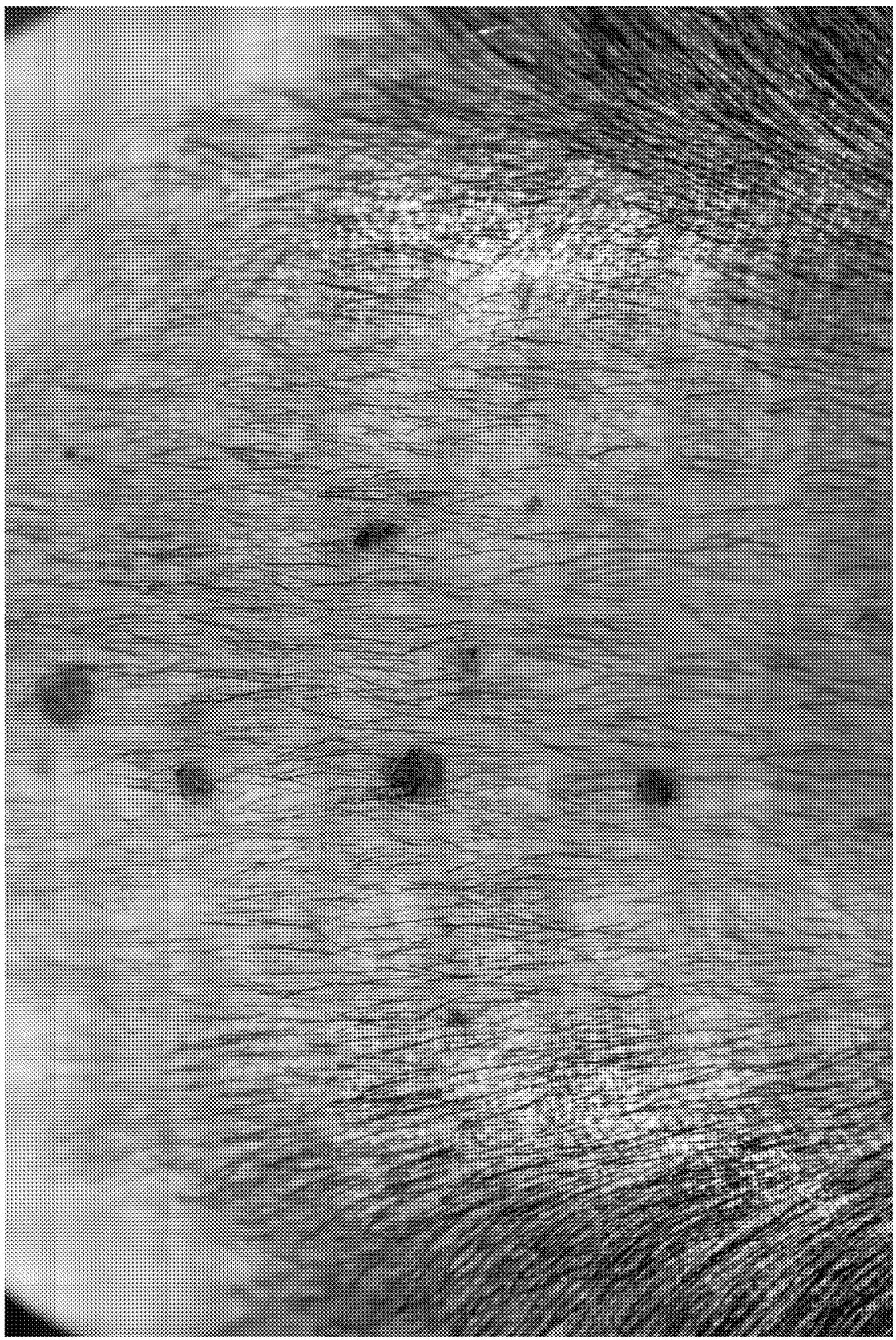
Figure 7G:
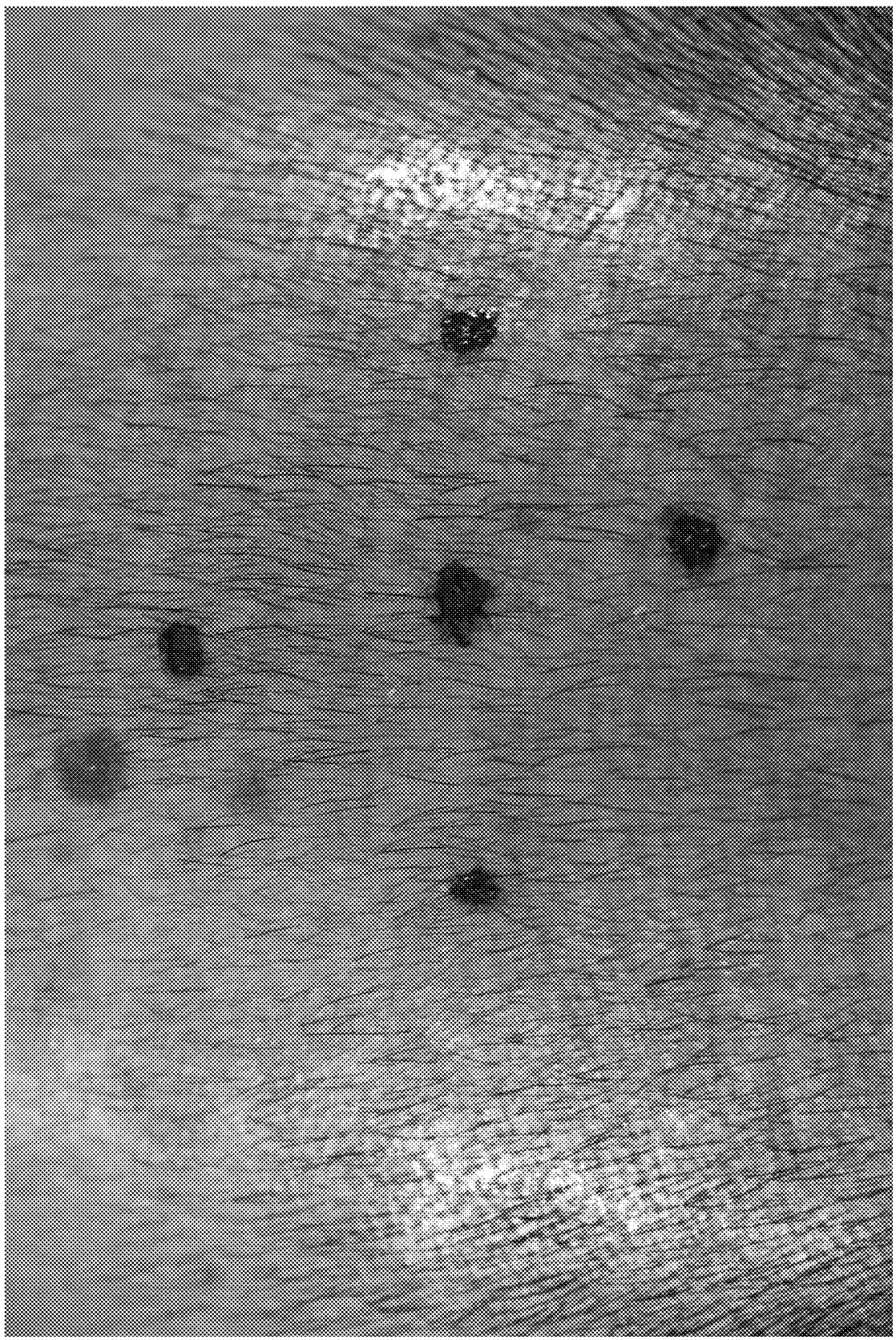
Figure 8A:
FIGS. 8A to 8L are a series of photographs showing the scalp of participant 8 prior to treatment and at intervals throughout the course of a six month treatment with a solution of 0.1% finasteride only.
Figure 8B:
Figure 8C:
Figure 8D:
Figure 8E:
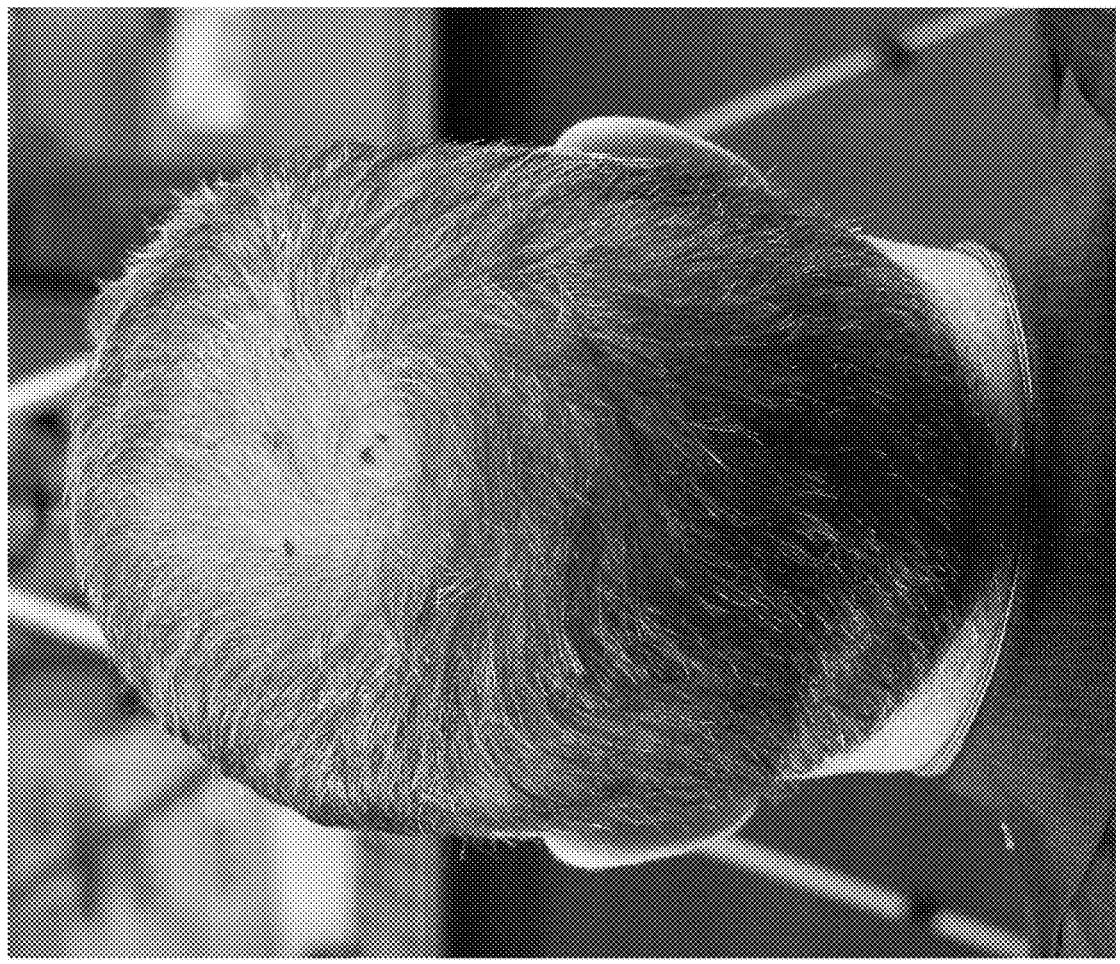
Figure 8F:
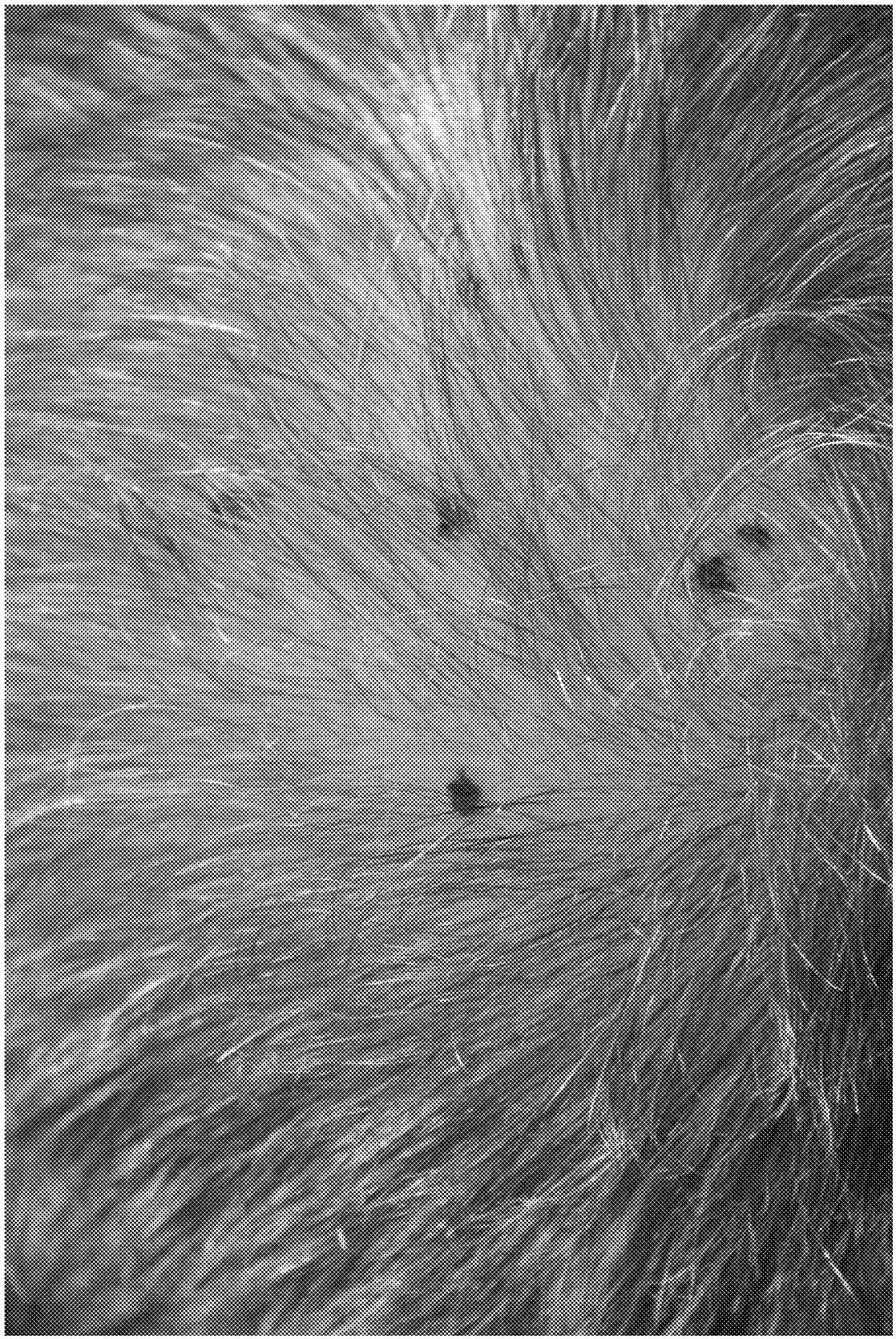
Figure 8G:
Figure 8H:
Figure 8I:
Figure 8J:
Figure 8K:
Figure 8L:

Four participants used a solution of 0.1% finasteride only. These participants were respectively 30 (participant 5), 33 (participant 6), 36 (participant 7) and 46 years of age (participant 8). FIGS. 5, 6, 7 and 8 show the results for participants 5, 6, 7 and 8 respectively. Only a slight improvement in hair regrowth is observed. The results are far inferior to those seen with the composition of the invention.

Figure 9A:
FIGS. 9A to 9L are a series of photographs showing the scalp of participant 9 prior to treatment and at intervals throughout the course of a six month treatment with a solution of 0.03% latanoprost only.
Figure 9B:
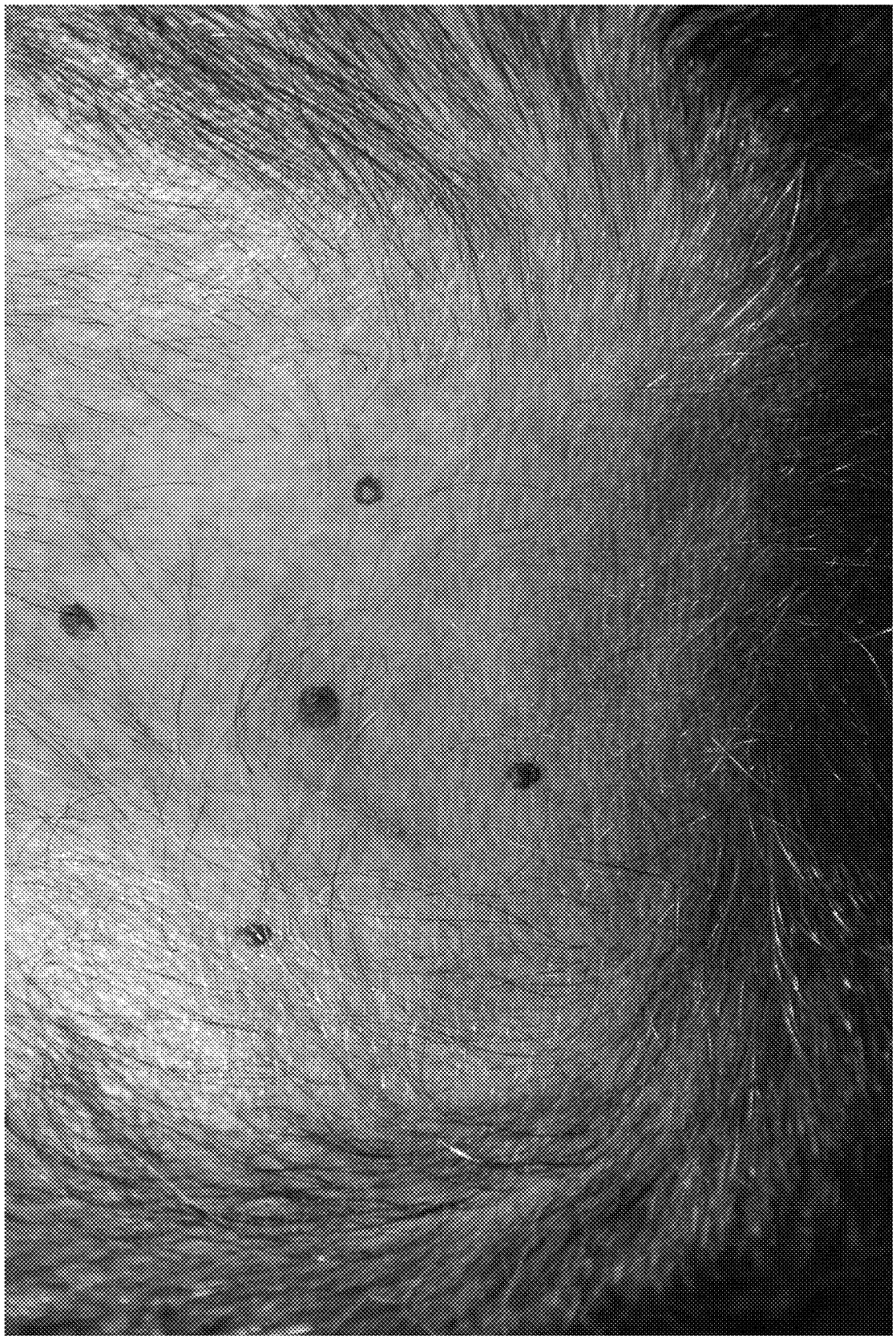
Figure 9C:
Figure 9D:
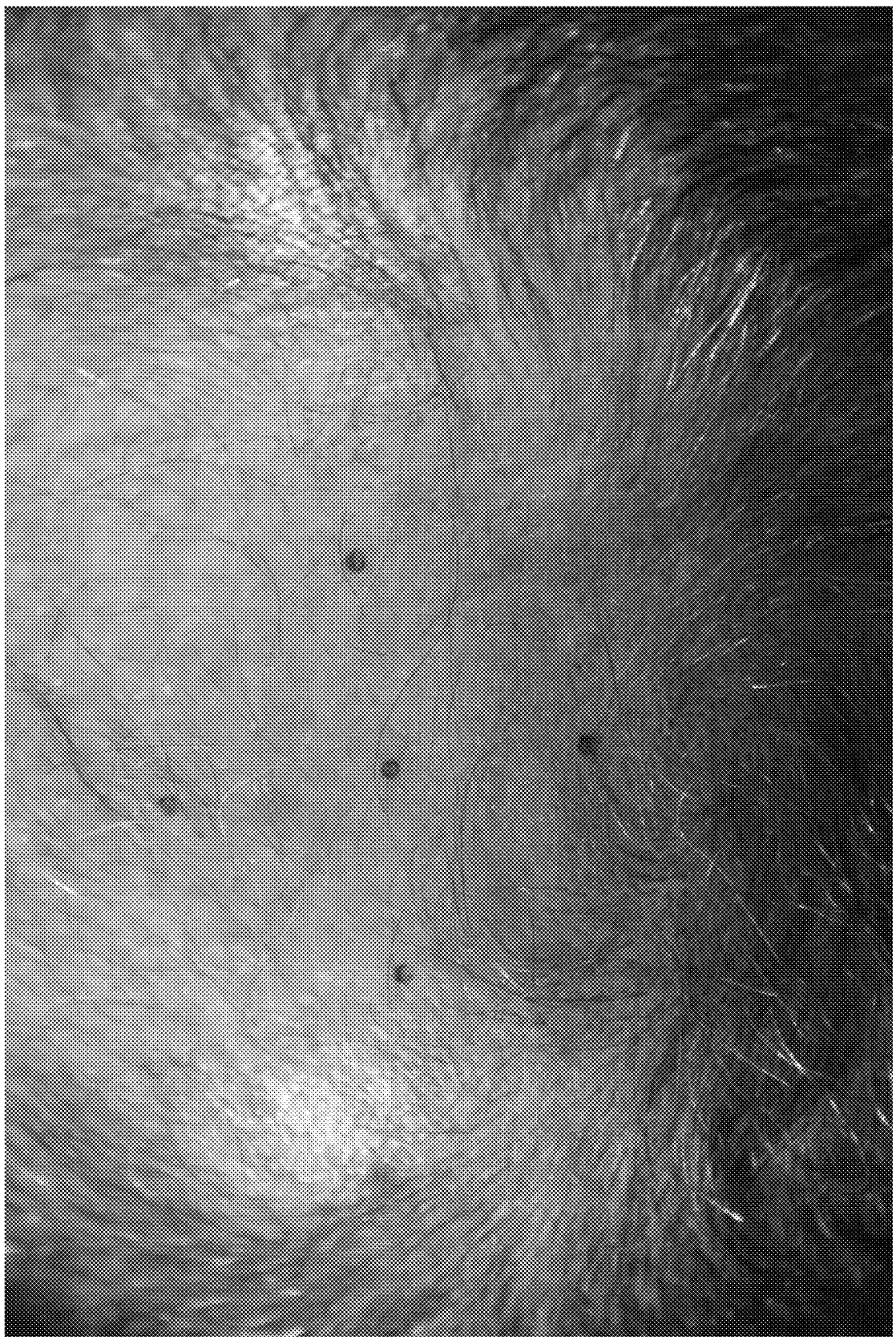
Figure 9E:
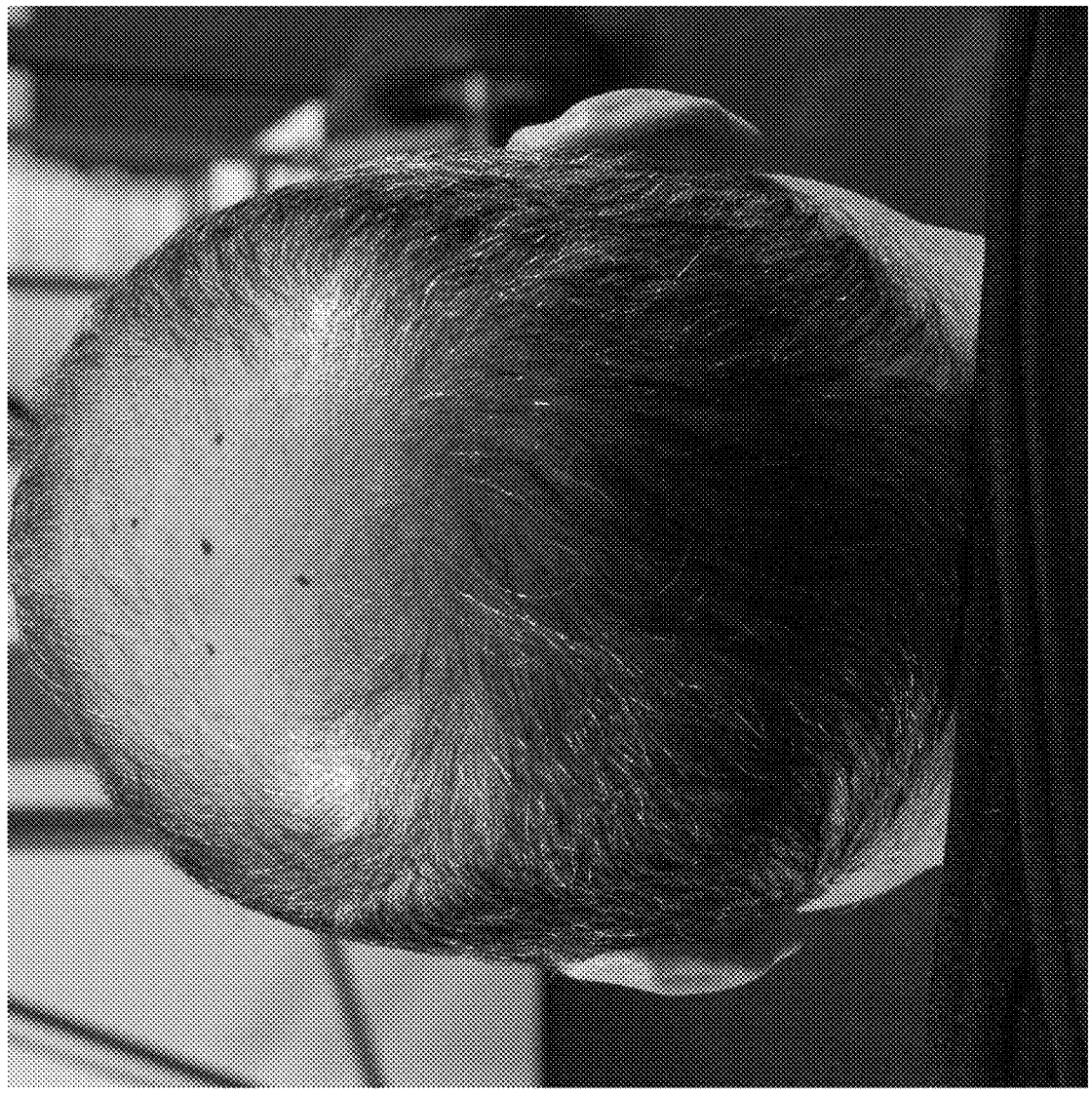
Figure 9F:
Figure 9G:
Figure 9H:
Figure 9I:
Figure 9J:
Figure 9K:
Figure 9L:
Figure 10A:
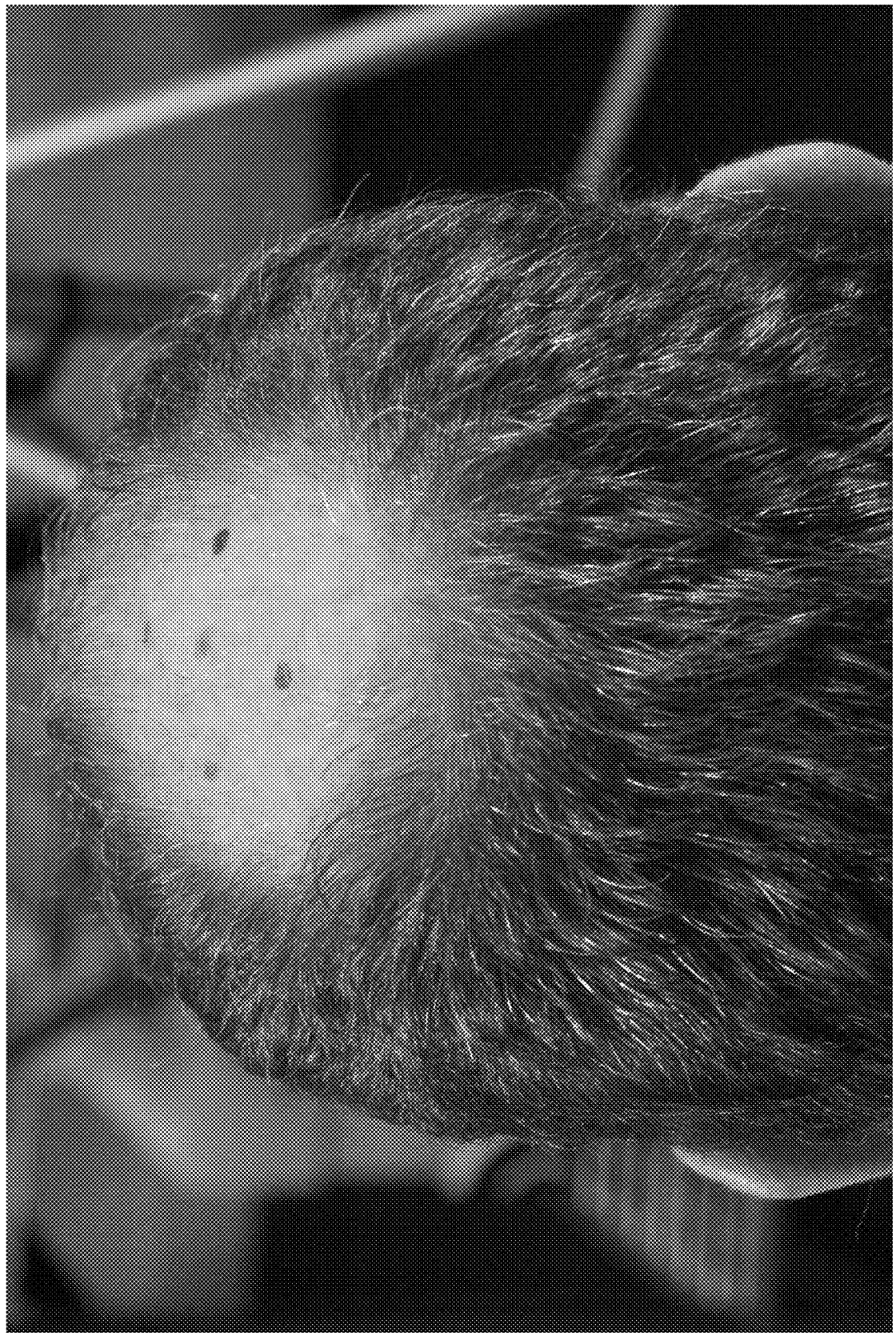
Figure 10B:
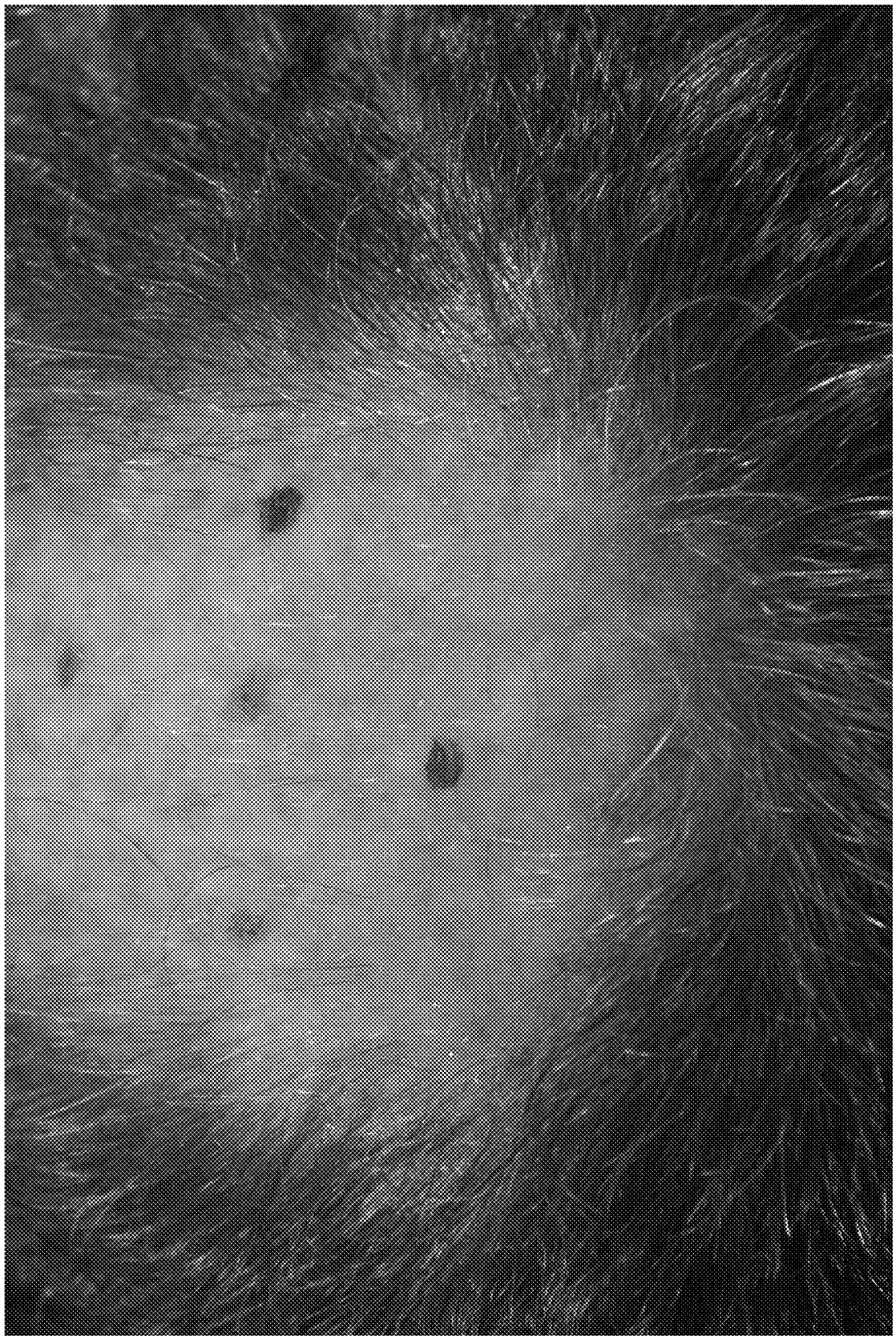
Figure 10C:
Figure 10D:
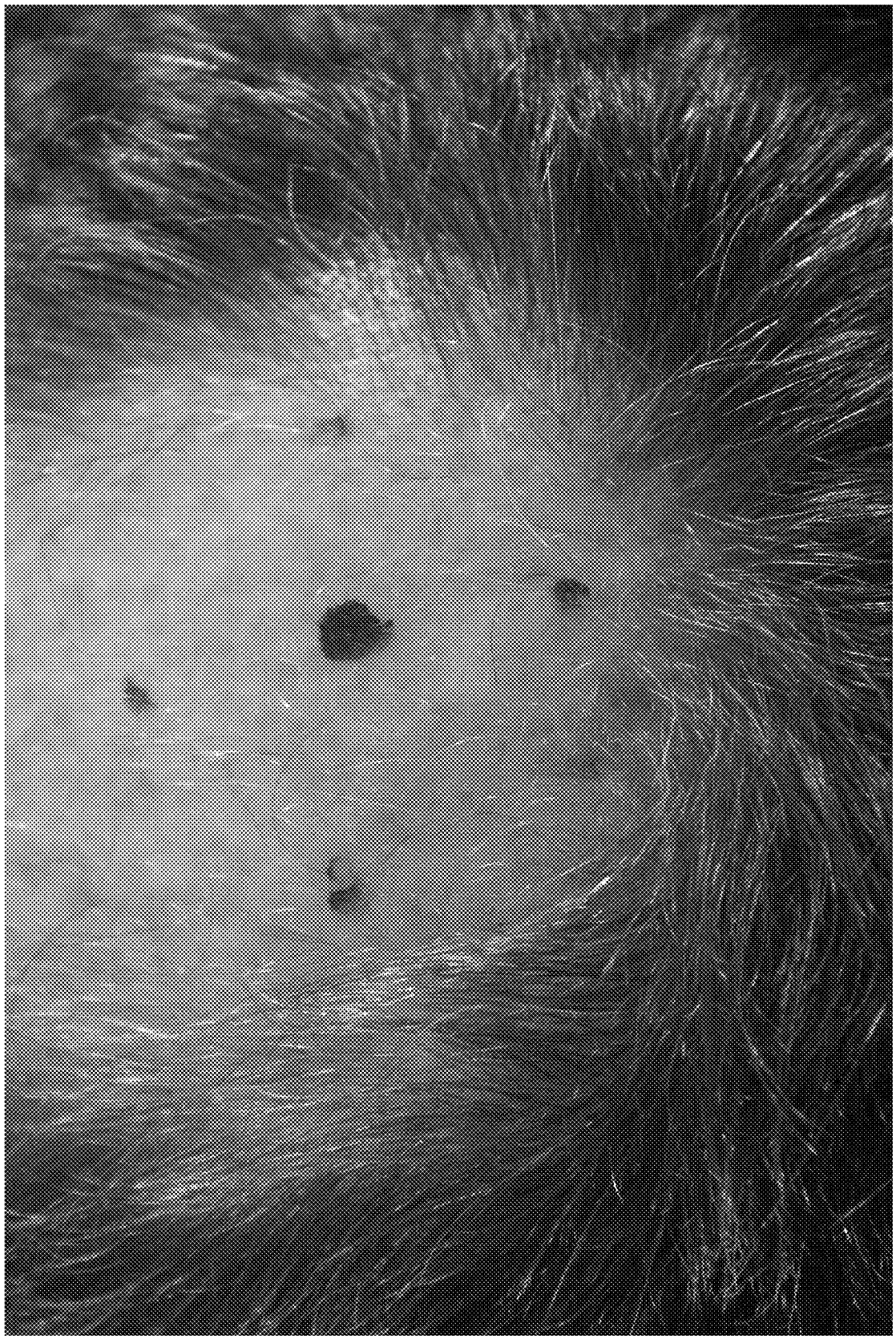
Figure 10E:
Figure 10F:
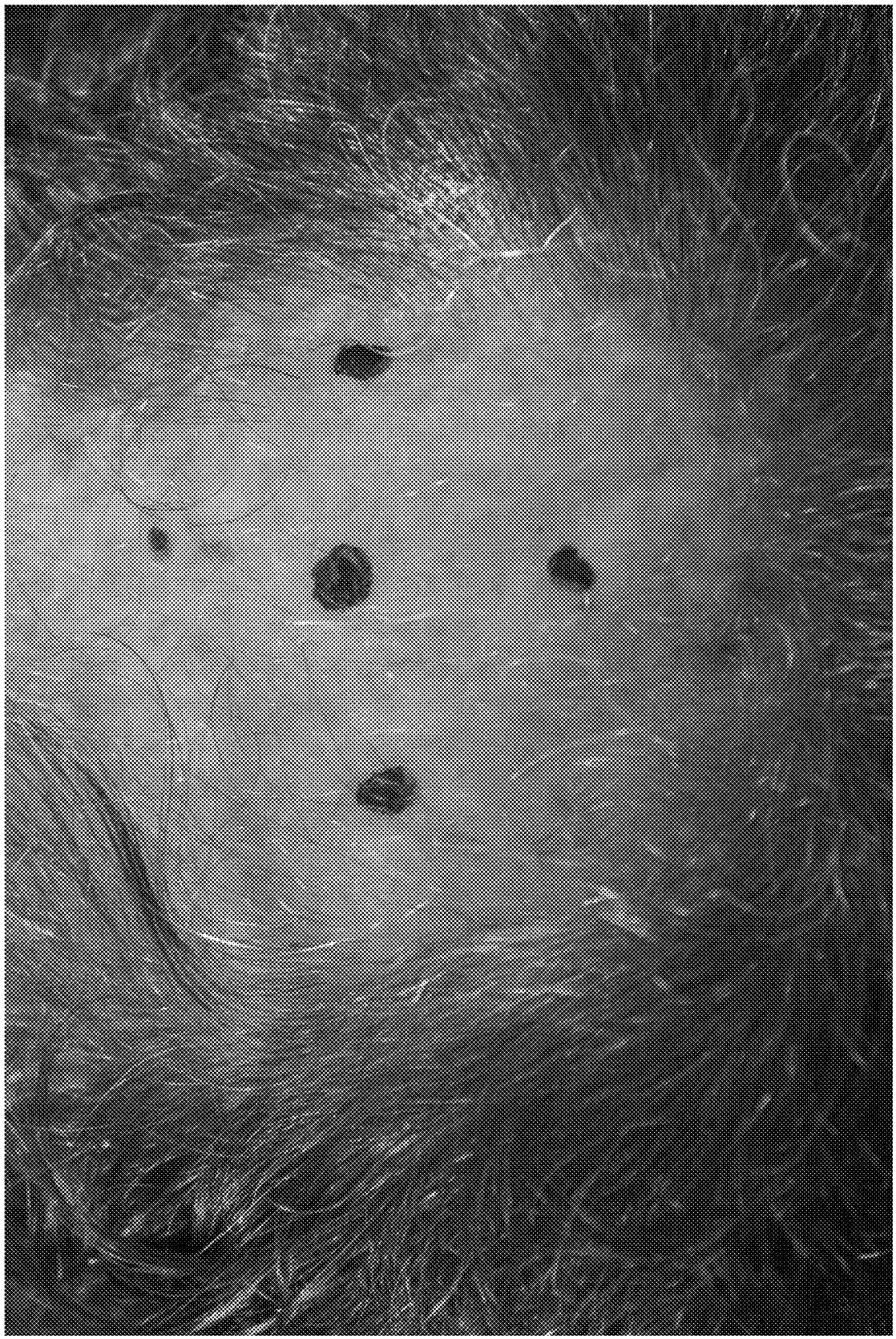
Figure 10G:
Figure 10H:
Figure 101:
Figure 10J:
Figure 10K:
Figure 10L:
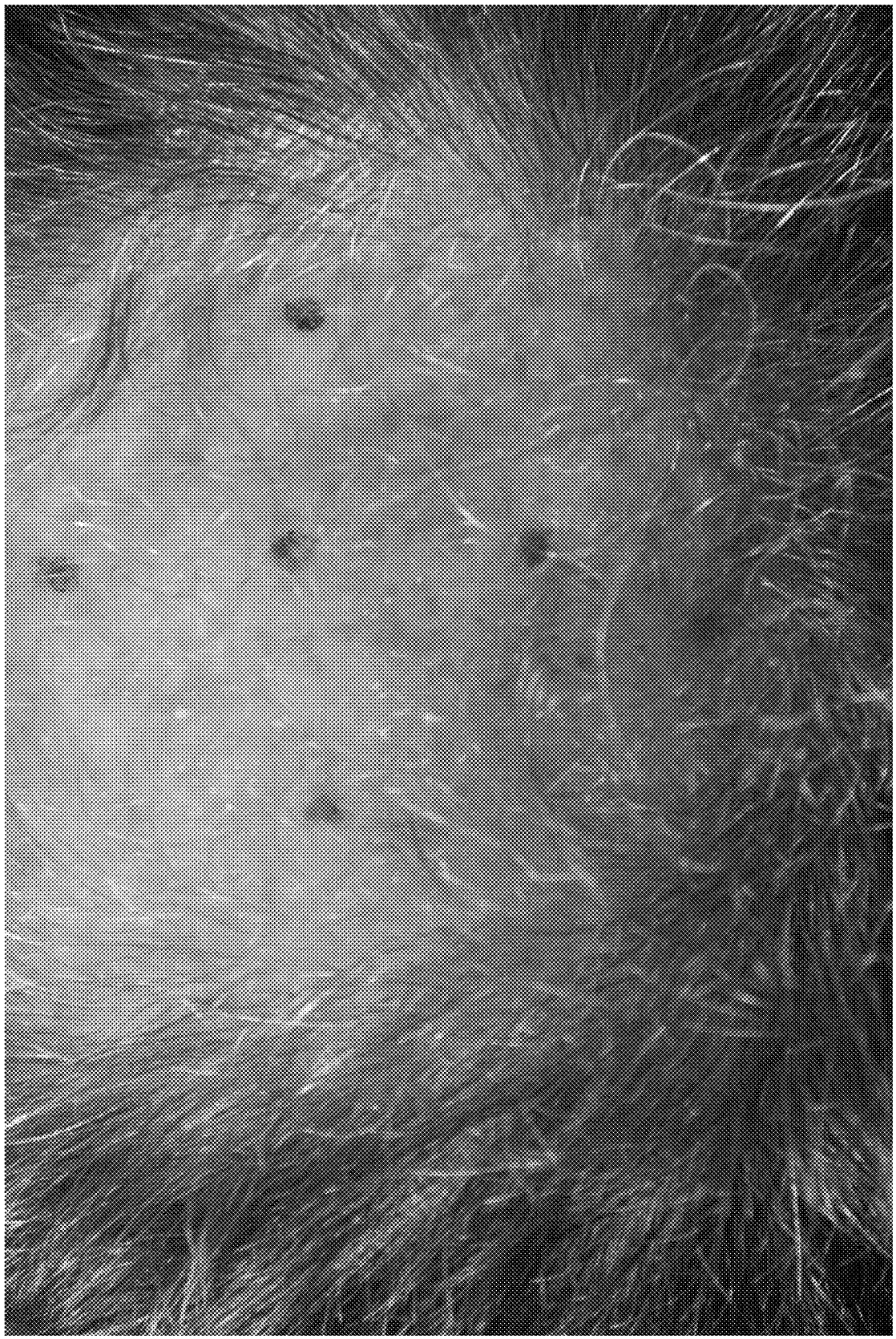

Two participants used a solution comprising 0.03% latanoprost only. These participants were respectively 48 (participant 9) and 52 (participant 10) years of age. FIGS. 9 and 10 show the results for participants 9 and 10 respectively. Only a slight improvement in hair regrowth was observed. The results obtained are far inferior to those observed with the composition of the invention.

The composition comprising minoxidil, finasteride and latanoprost shows improved properties in terms of reduction of hair loss and increase of regrowth of hair when compared to a solution of 5% minoxidil alone, a solution of 0.1% finasteride alone or a solution of 0.03% latanoprost alone. The improvements shown in the reduction of hair loss and the increase of regrowth hair for the composition of the invention are superior to the improvements seen for each of the components of the composition taken individually and the results obtained to date suggest that the improvements may be superior to those of the sum of the said components.

While the composition of the invention has been tested on males, similar results are expected on females as the mechanism of hair growth is the same for both genders.

While a composition of the invention comprising a specific 5α-reductase inhibitor, namely finasteride, has been tested, it is surmised that other 5α-reductase inhibitors, will work in the same manner as finasteride. Inhibitors of form II of 5α-reductase are most preferred as the type II form of 5α-reductase is found predominantly in the hair follicles. It is also surmised that androgen receptor antagonists have an effect similar to that of finasteride in that they would lead to a decrease in the levels of DHT.

While the present invention has been described in connection with specific embodiments thereof and in a specific use, various modifications will occur to those skilled in the art. The scope of the claims should not be limited by the preferred embodiments or the examples but should be given the broadest interpretation consistent with the description as a whole.

What is claimed is:

1. A topical composition, comprising:
   (a) 2% to 5% minoxidil;
   (b) finasteride in an amount greater than or equal to 0.01% and less than 0.225%; and
   (c) 0.01% to 0.15% latanoprost,
wherein the topical composition is for topical application to a scalp.

2. The composition according to claim 1, wherein the composition comprises at least 0.05% finasteride.

3. The composition according to claim 1, wherein the composition comprises 0.03% to 0.15% latanoprost.

4. The composition according to claim 1, wherein the composition comprises 3% to 5% minoxidil.

5. A composition for use in reducing hair loss or increasing regrowth of hair in a human subject, the composition comprising:
   (a) 2% to 5% minoxidil;
   (b) finasteride in an amount greater than or equal to 0.01% and less than 0.225%; and
   (c) 0.01% to 0.15% latanoprost.

6. The composition according to claim 5, wherein the composition comprises at least 0.05% finasteride.

7. The composition according to claim 5, wherein the composition comprises 0.03% to 0.15% latanoprost.

8. The composition according to claim 5, wherein the composition comprises 3% to 5% minoxidil.

9. The composition according to claim 5, wherein the human subject is a male.

10. The composition according to claim 5, wherein the human subject is a female.

11. The composition according to claim 5, wherein said composition is for topical administration.

12. The composition according to claim 11, wherein the composition is in the form of a spray.

13. The composition of claim 1, wherein the composition is in the form of a spray.

* * * * *